US010047376B2

(12) United States Patent
West

(10) Patent No.: US 10,047,376 B2
(45) Date of Patent: Aug. 14, 2018

(54) TRANSGENIC ANIMALS WITH CUSTOMIZABLE TRAITS

(71) Applicant: MICE WITH HORNS, LLC, Delray Beach, FL (US)

(72) Inventor: James West, Nashville, TN (US)

(73) Assignee: AGGENETICS, INC., Nashville, TN (US)

( * ) Notice: Subject to any disclaimer, the term of this patent is extended or adjusted under 35 U.S.C. 154(b) by 414 days.

(21) Appl. No.: 13/943,081

(22) Filed: Jul. 16, 2013

(65) Prior Publication Data

US 2013/0298268 A1 Nov. 7, 2013

Related U.S. Application Data

(63) Continuation of application No. 13/768,760, filed on Feb. 15, 2013, now abandoned.

(60) Provisional application No. 61/598,987, filed on Feb. 15, 2012.

(51) Int. Cl.
| | | |
|---|---|---|
| *A01K 67/00* | (2006.01) | |
| *A01K 67/033* | (2006.01) | |
| *C12N 15/85* | (2006.01) | |
| *A01K 67/027* | (2006.01) | |

(52) U.S. Cl.
CPC ...... *C12N 15/8509* (2013.01); *A01K 67/0275* (2013.01); *A01K 2217/05* (2013.01); *A01K 2217/203* (2013.01); *A01K 2217/206* (2013.01); *A01K 2227/10* (2013.01); *A01K 2267/02* (2013.01); *A01K 2267/03* (2013.01)

(58) Field of Classification Search
CPC .................................................. A01K 67/0275
See application file for complete search history.

(56) References Cited

U.S. PATENT DOCUMENTS

2011/0265192 A1  10/2011  Bolund et al.

OTHER PUBLICATIONS

Bosenberg, 2006, Genesis, 44:262-267.*
Kanatsu-Shinohara, Biology of Reproduction, 2004, 71:1202-1207.*
Albuquerque, 2007, ARVO, 48:4454.*
Kalluri, AAPS PharmSciTech, 12:431-441).*
Gitton (BMC Biotechnology 2009, 9:1-11).*
Herwaskar, Drug Discovery Today:Technologies, 2012, 9:e147-e154.*
Choi, Journal of Controlled Release, 2012, 157:272-278.*
Banga (Biological Barriers to Protein Delivery, edited by Kenneth L. Audus and Thomas 1. Raub. Plenum Press, New York, 1993; Chapter 8, pp. 179-197).*
Chrostek, Anna et al., "Rac1 is Crucial for Hair Follicle Integrity but Is Not Essential for Maintenance of the Epidermis," *Molecular and Cellular Biology*, Sep. 2006, 26(18):6957-6970.
Giménez, Estela et al., "A Transgenic Mouse Model with Inducible Tyrosinase Gene Expression Using the Tetracycline (Tet-on) System Allows Regulated Rescue of Abnormal Chiasmatic Projections Found in Albinism," *Pigment Cell Res*, 2004, 17:363-370.
Indra, Arup Kumar et al., "Temporally-controlled site-specific mutagenesis in the basal layer of the epidermis: comparison of the recombinase activity of the tamoxifen-inducible Cre-ER$^T$ and Cre-ER$^{T2}$ recombinases," *Nucleic Acids Research*, 1999, 27(22):4324-4327.
Mardaryev, Andrei N. et al., "Micro-RNA-31 controls hair cycle-associated changes in gene expression programs of the skin and hair follicle," *The FASEB Journal*, 2010, 24:3869-3881.
Mukhopadhyay, Anandaroop et al., "Activated Kras Alters Epidermal Homeostasis of Mouse Skin, Resulting in Redundant Skin and Defective Hair Cycling," *J. Invest. Dermatol.*, Feb. 2011, 131(2):311-319.
Supplementary European Search Report dated Sep. 9, 2015, for related European Application No. 13748835.9, in which references R1-R5 were cited.
Hearing, Vincent J. et al., "Enzymatic control of pigmentation in mammals," *FASEB J.*, 1991, 5:2902-2909.
Hellström, Anders R. et al., "Inactivation of Pmel Alters Melanosome Shape But Has Only a Subtle Effect on Visible Pigmentation," *PLos Genetics*, Sep. 2011, 7(9):1-16.
Hou, Ling et al., "Interspecies difference in the regulation of melanocyte development by SOX10 and MITF," *PNAS*, Jun. 13, 2006, 103(24):9081-9085.
McGlinchey, Ryan P. et al., "The repeat domain of the melanosome fibril protein Pmel17 forms the amyloid core promoting melanin synthesis," *PNAS*, Aug. 18, 2009, 106(33):13731-13736.
Mundy, Nicholas I. "A window on the genetics of evolution: MC1R and plumage colouration in birds," *Proc. R. Soc. B.*, 2005, 272:1633-1640.
Behrendt, K. et al., "A function for Rac1 in the terminal differentiation and pigmentation of hair," *Journal of Cell Science*, Jan. 24, 2012, vol. 125, p. 896-905.
Candille S. et al., "A β-defensin mutation causes black coat color in domestic dogs." *Science*, Nov. 30, 2007, vol. 318(5855), p. 1418-1423.
Gonzalez-Gonzalez, E. et al., "siRNA silencing of keratinocyte-specific GFP expression in a transgenic mouse skin model," *Gene Therapy*, May 28, 2009, vol. 16(8), p. 963-972.
Kistner, A. et al., "Doxycycline-mediated quantitative and tissue-specific control of gene expression in transgenic mice," *Proc.Nat. Acad. Sci.U.S.A.*, Oct. 1996, vol. 93, p. 10933-10938.

(Continued)

*Primary Examiner* — Valerie E Bertoglio
(74) *Attorney, Agent, or Firm* — Saliwanchik, Lloyd & Eisenschenk

(57) ABSTRACT

Disclosed are materials and methods for creating customizable traits in animals. In the demonstration of the principle of the subject invention, a keratin-14 specific promoter is used with, red fluorescent protein in the loxp cassette, dominant black (ΔG23) beta defensin 103 in the pigment cassette, and an SV40 (with intron) polyadenylation sequence. When Cre recombinase (or HTNCre) is applied to the animal's skin in a carrier base (e.g., lipid bilayers), fur is permanently genetically modified to turn black in the shape in which it was applied.

3 Claims, 4 Drawing Sheets

(56) References Cited

OTHER PUBLICATIONS

Liang, C. et al., "Transgenic mice exhibiting inducible and spontaneous Cre activities driven by a bovine keratin 5 promoter that can be used for the conditional analysis of basal epithelial cells in multiple organs," *Journal of Biomedical Science*, Jan. 8, 2009, vol. 16(2), p. 1-8.

Nagy, A., "Cre-Recombinase: The universal reagent for genome tailoring." *Genesis*, 2000, vol. 26, p. 99-109.

Nolden L et al., "Site-specific recombination in human embryonic stem cells induced by cell-permanent Cre recombinase," *Nature Methods*, Jun. 2006, vol. 3(6), p. 461-467.

Rae, J. et al., "V600EBraf::Tyr-CreERT2::K14-Kitl Mice Do Not Develop Superficial Spreading-Like Melanoma: Keratinocyte Kit Ligand Is Sufficient to "Translocate" $^{V600E}$Braf-Driven Melanoma to the Epidermis", *Journal of Investigative Dermatology*, Nov. 24, 2011, vol. 132, p. 488-491.

Chang, Hung-Shu et al., "Using siRNA Technique to Generate Transgenic Animals with Spatiotemporal and Conditional Gene Knockdown." *Molecular Pathogenesis of Genetic and Inherited Diseases*, Nov. 2004, 165(5): 1535-1541.

Notice of Reasons for Rejection dated Nov. 7, 2016, for corresponding Japanese Application No. 2014-557821, in which reference R1 was cited.

Schmutz, Sheila M., Dreger, Dayna L., "Interaction of MC1R and PMEL alleles on solid coat colors in Highland cattle." *Animal Genetics*, Feb. 2013, 44(1): 9-13.

\* cited by examiner

SEQUENCE LISTING

```
<160> NUMBER OF SEQ ID NOS: 19

<210> SEQ ID NO 1
<211> LENGTH: 608
<212> TYPE: PRT
<213> ORGANISM: Acyrthosiphon pisum

<400> SEQUENCE: 1

Met Leu Thr Tyr Ile Asp Val His Phe Ile Tyr Thr Leu Pro Val Val
1               5                   10                  15

Ala Val Leu Ala Leu Ile Thr Trp Pro Phe Ile Ser Arg Leu Glu Leu
            20                  25                  30

Phe Lys Ile Gly Phe Val Cys Thr Met Ala Phe Val Tyr Thr Thr Pro
        35                  40                  45

Trp Asp Asn Tyr Ile Ile Phe His Asn Ala Trp Met Tyr Lys Pro Lys
    50                  55                  60
```

```
Asn Ile Leu Ala Val Ile Gly Tyr Val Pro Val Glu Glu Tyr Met Phe
 65                  70                  75                  80

Phe Val Ile Gln Thr Leu Met Thr Ser Leu Trp Ala Leu Val Phe Thr
             85                  90                  95

Arg Trp Ser Pro Ala Cys Phe Asn Phe Asn Lys Thr Ser Tyr
                100             105            110

Thr Leu Ile Arg Trp Ile Pro Ile Leu Ala Leu Val Met Thr Thr Ile
        115                 120                 125

Gln Gly Tyr Asn Ile Ala Val Pro Gly Lys Asn Thr Phe Tyr Leu Gly
    130                 135                 140

Cys Ile Met Trp Trp Ser Cys Pro Val Ile Met Phe Leu Trp Tyr Gly
145                 150                 155                 160

Ala Gly Asn Tyr Phe Val Lys Lys Ser Thr Ser Ala Ile Ala Val
                165             170             175

Ile Val Pro Thr Leu Tyr Leu Cys Trp Val Asp Arg Ile Ala Leu Lys
            180             185             190

Asp Asp Val Trp His Ile Asn Glu Lys Thr Ser Leu Asn Ile Phe Val
            195             200             205

Val Asp Asp Leu Pro Phe Glu Glu Cys Leu Phe Leu Ile Thr Asn
210                 215                 220

Val Ile Ile Val Leu Gly Gly Met Ala Phe Asp Lys Ser Tyr Gly Leu
225                 230                 235                 240

Ala Asp Thr Tyr Thr Phe Glu Phe Pro Leu Arg Tyr Ser Ser Ser Trp
                245             250             255

Lys Tyr Tyr Ser Gln Gln Met Gln Gln Phe Val Arg Ala Glu Cys Asp
            260             265             270

Met Ser Pro Ser Pro Val Asn Asp Ile Arg Gln Cys Leu Asn Val Leu
            275             280             285

Lys Arg Ala Ser Lys Ser Phe Asn Val Ala Ser Leu Val Phe Pro Ala
            290             295             300

Gly Val Arg Leu His Leu Ile Ile Leu Tyr Ala Phe Cys Arg Val Thr
305                 310             315                 320

Asp Asp Met Ile Asp Ser Glu Pro Lys Val Gly Val Lys Lys Gln Lys
                325             330             335

Leu Lys Leu Ile Glu Thr Phe Ile Asp Glu Leu Phe Ala Asp Arg Ser
            340             345             350

Ala Asp Tyr Asp Val Lys Thr Ser Met Thr Pro Arg Lys Pro Glu Val
        355             360             365

Lys Trp Glu Gln Tyr Arg Leu Asp Leu Thr Asp Glu Leu Ser Cys
    370             375             380

Phe Arg Ala Ile Ser Arg Ile Ser Phe Tyr Leu Pro Arg Lys Pro Phe
385             390             395             400

Tyr Glu Leu Leu Asp Gly Tyr Arg Trp Asp Val Asp Gly Lys Thr Val
                405             410             415

Gln Asn Glu Thr Asp Leu Leu Leu Tyr Ser Ser Tyr Val Ala Gly Ser
            420             425             430

Val Gly Thr Leu Cys Val Tyr Val Met Val Tyr Lys Ser Gly Thr Gln
            435             440             445

Ile Asp Asp Asp Lys Arg His Asp Phe Val Ile Gly Lys Ala Gln Gln
    450             455             460

Met Gly Gln Val Leu Gln Ile Val Asn Ile Ser Arg Asp Ile Val Thr
465             470             475             480
```

-continued

```
Asp Ser Glu Thr Leu Gly Arg Cys Tyr Val Pro Ala Glu Tyr Met Asp
            485                 490                 495

Asn Ala Ala Val Val Asn Thr Leu Cys Ser Asp Arg Asp Pro Trp
        500                 505                 510

Thr Leu Gly Ser Glu Lys Leu Lys Ser Tyr Ala Thr Arg Met Ile Arg
            515                 520                 525

Leu Ala Asn Arg Tyr Gln Leu Glu Ser Leu Glu Gly Ile Arg Tyr Leu
    530                 535                 540

Pro Tyr Glu Val Arg Gly Pro Val Leu Val Ala Thr Asp Ile Tyr Arg
545                 550                 555                 560

Gly Val Ala Cys Ala Val Glu Ala Ser Pro Thr Tyr Pro Arg Arg Ala
                565                 570                 575

Ser Leu Gly Lys Trp Asp Lys Ile Leu Val Ser Ile Asn Ser Leu Tyr
            580                 585                 590

Phe Lys Ser Leu Lys Tyr Phe Phe Gln Ala Asp Arg Cys Lys His Cys
        595                 600                 605

<210> SEQ ID NO 2
<211> LENGTH: 588
<212> TYPE: PRT
<213> ORGANISM: Acyrthosiphon pisum

<400> SEQUENCE: 2

Met Leu Thr Tyr Ile Gly Ala His Leu Ser Tyr Thr Leu Pro Val Ile
1               5                   10                  15

Gly Val Leu Thr Leu Ile Thr Arg Pro Phe Ile Asn Arg Leu Glu Ile
            20                  25                  30

Phe Lys Ile Gly Phe Ile Ser Gly Leu Ala Val Ile Tyr Thr Ile Pro
        35                  40                  45

Trp Tyr Ser Tyr Phe Val Tyr Asn His Gly Ala Arg Tyr Ser Pro
    50                  55                  60

Gly Ala Val Leu Ala Val Val Gly Asn Val Pro Val Glu Glu Tyr Met
65                  70                  75                  80

Phe Val Val Met Gln Thr Val Leu Thr Ser Leu Trp Ala Leu Met Phe
                85                  90                  95

Val Gln Trp Ser Thr Pro Cys Leu Asn Phe Asn Tyr Asp Lys Arg Ser
            100                 105                 110

Tyr Gln Leu Ile Arg Trp Ile Pro Ile Ser Leu Leu Thr Val Val Thr
        115                 120                 125

Ala Val Gly Tyr Ala Met Ala Val Arg Gly Gln Glu Thr Phe Tyr Leu
    130                 135                 140

Gly Ser Ile Leu Cys Trp Ala Ser Pro Ala Ile Ala Ile Met Trp Tyr
145                 150                 155                 160

Gly Ala Gly Asn Phe Phe Ala Lys Lys Ile Ile Pro Ser Ser Ile Ala
                165                 170                 175

Ile Ala Gly Pro Thr Leu Tyr Met Cys Trp Ile Asp Arg Met Ala Val
            180                 185                 190

Ser Asp Asp Asn Asn Asp Ser Gly Lys Leu Ala Pro Glu Asp Ala Leu
        195                 200                 205

Phe Val Phe Val Thr Asn Leu Met Val Val Leu Ala Gly Ser Ser Tyr
    210                 215                 220

Asp Lys Ala Tyr Gly Met Ile Val Thr Tyr Ser Leu Asp Phe Pro His
225                 230                 235                 240

Gln Phe Ser Val Ser Cys Arg Phe Val Arg Gln Met Leu Arg Ala Phe
                245                 250                 255
```

Met Thr Ser Glu Tyr Ala Thr Pro Ser Ala Val Thr Gln Asp Ile Lys
                260                 265                 270

Thr Ser Ile Lys Val Leu Ser Thr Ser Asn Ala Phe Gly Thr Ser Asn
            275                 280                 285

Tyr Leu Phe His Ala Gly Ile Arg Leu Asp Leu Ile Ile Leu Tyr Ala
        290                 295                 300

Phe Cys Arg Val Thr Asp Glu Met Phe Asp Ser Lys Ser Asp Glu Lys
305                 310                 315                 320

Lys Lys Lys Leu Lys Leu Glu Leu Ser Lys Gln Phe Ile Ser Glu Val
                325                 330                 335

Phe Ala Asp Arg Lys Ser Asp Tyr Asp Val Lys Lys Thr Pro Gln Glu
            340                 345                 350

Val Lys Ile Asp Trp Lys Lys Tyr Glu Ser Glu Phe Thr Asp Val Glu
        355                 360                 365

Leu Ser Ser Tyr Arg Ala Val Ser Arg Ile Ala Phe Phe Leu Pro Arg
    370                 375                 380

Lys Pro Phe Glu Glu Leu Phe Ala Gly Tyr Gln Trp Asp Leu Glu Phe
385                 390                 395                 400

Thr Leu Val Arg Asn Glu Lys Asp Leu Met Leu Tyr Thr Thr Tyr Val
                405                 410                 415

Ala Gly Ser Ile Gly Ala Met Cys Leu Tyr Val Ile Met Tyr Arg Tyr
            420                 425                 430

Gly Asn Asp Met Asn Asp Leu Val Asp Lys Ala Asp Tyr Leu Thr Lys
        435                 440                 445

His Ala Tyr Lys Ile Gly Gln Gly Leu Gln Leu Val Asn Ile Ala Arg
    450                 455                 460

Asp Leu Val Ser Asp Ser Glu Ser Leu Gly Arg Cys Tyr Phe Pro Ala
465                 470                 475                 480

Glu Tyr Met Asp Asp Glu Lys Glu Asp Leu Arg Ile Leu Cys Lys Glu
                485                 490                 495

Lys Asn Pro Arg Ser Leu Gly Asn Lys Lys Leu Lys Lys Tyr Ser Ser
            500                 505                 510

Lys Met Ile Gln Leu Ala Asn Lys Gln Gln Phe Glu Ser Met Gly Ala
    515                 520                 525

Ile Lys Tyr Leu Pro Gln Asp Leu Ile Gly Ser Val Leu Ala Ser Thr
530                 535                 540

Glu Met Tyr Arg Gly Leu Ile Lys Ala Ile Gln Ser Cys Pro Thr Tyr
545                 550                 555                 560

Pro Thr Arg Ala Ser Leu Pro Lys Leu Ser Lys Leu Leu Ile Val Leu
                565                 570                 575

Asn Thr Leu Tyr Ile Lys Ser Ile Gln Tyr Ile Phe
            580                 585

<210> SEQ ID NO 3
<211> LENGTH: 589
<212> TYPE: PRT
<213> ORGANISM: Acyrthosiphon pisum

<400> SEQUENCE: 3

Met Leu Thr Tyr Ile Asp Phe His Leu Lys Tyr Thr Leu Thr Val Ile
1               5                   10                  15

Gly Val Leu Ser Leu Ile Ala Arg Pro Phe Ile Asn Arg Ser Glu Val
            20                  25                  30

Phe Lys Ile Ala Phe Ile Ser Ala Ile Ala Phe Val Tyr Thr Thr Pro

```
            35                  40                  45
Trp Asp Asn Tyr Val Ile Tyr Ser Asp Ala Trp Asn Tyr Pro Leu Asp
    50                  55                  60

Arg Val Leu Ala Thr Ile Gly Tyr Val Pro Ile Glu Glu Tyr Met Phe
65                  70                  75                  80

Phe Ile Ile Gln Thr Val Leu Thr Ser Leu Trp Ala Leu Leu Cys Val
                85                  90                  95

Arg Trp Ser Thr Pro Cys Leu Asn Phe Asn Tyr Asp Lys Arg Ser Tyr
                100                 105                 110

Gln Leu Ile Arg Trp Val Pro Ile Thr Ile Leu Ala Ile Val Thr Ile
                115                 120                 125

Val Gly Tyr Lys Leu Val Ile Pro Gly Gln Gly Thr Phe Tyr Leu Gly
                130                 135                 140

Cys Ile Leu Cys Trp Val Ser Pro Val Ile Ile Phe Leu Trp Tyr Gly
145                 150                 155                 160

Ala Gly Asn Phe Phe Val Lys Lys Ile Ile Pro Ser Thr Phe Ala Ile
                165                 170                 175

Val Val Pro Ser Leu Tyr Leu Cys Trp Ile Asp Gln Leu Ala Leu Lys
                180                 185                 190

Glu Asn Val Trp His Ile Asn Glu Lys Thr Ser Leu Asn Ile Phe Ile
                195                 200                 205

Val Asp Asp Leu Pro Ile Glu Glu Ala Phe Phe Phe Val Val Asn
                210                 215                 220

Leu Ile Ile Val Leu Val Gly Ala Cys Phe Asp Lys Ala Ser Gly Val
225                 230                 235                 240

Ile Glu Thr Tyr Thr Ser Glu Tyr Pro Leu Arg Phe Ser Ile Ser Trp
                245                 250                 255

Lys Tyr Val Cys Gln Leu Phe Ser Ala Phe Ala Thr Ser Glu Tyr Asn
                260                 265                 270

Met Pro His Ile Val Thr Glu Asp Ile Lys Glu Ser Ile Glu Ile Ile
                275                 280                 285

Thr Val Ala Ser Lys Ser Phe Thr Thr Ala Ser Phe Leu Phe Pro Ala
                290                 295                 300

Gly Ile Arg Leu Asp Leu Ile Ile Leu Tyr Ser Phe Cys Arg Val Thr
305                 310                 315                 320

Asp Asp Met Ile Asp Asp Glu Leu Asp Val Glu Lys Lys Arg Lys
                325                 330                 335

Phe Glu Leu Thr Glu Arg Phe Ile Lys Glu Leu Phe His Asp Arg Lys
                340                 345                 350

Ser Asp Tyr Asp Val Gln Thr Lys Pro Gln Glu Leu Lys Ile Asp Trp
                355                 360                 365

Thr Lys Tyr Glu Ser Glu Leu Thr Asp Arg Glu Met Ser Cys Phe Arg
                370                 375                 380

Ala Leu Ser Arg Ile Ala Phe Tyr Leu Pro Arg Lys Pro Phe Asp Glu
385                 390                 395                 400

Leu Leu Ala Gly Tyr Lys Trp Asp Ile Glu Gly Arg Leu Ile Arg Asn
                405                 410                 415

Glu Asp Asp Leu Leu Leu Tyr Ser Thr Tyr Val Ala Gly Ser Val Gly
                420                 425                 430

Ala Leu Cys Val Tyr Val Met Met Tyr Arg Cys Asp Asn Asp Lys Tyr
                435                 440                 445

Asp Leu Val Glu Asn Tyr Asp Tyr Val Ile Glu Lys Ala Tyr Gln Met
450                 455                 460
```

Gly Arg Ala Leu Gln Leu Val Asn Ile Ala Arg Asp Ile Val Thr Asp
465                 470                 475                 480

Ser Glu Thr Leu Gly Arg Cys Tyr Val Pro Thr Glu Tyr Met Asp Asp
                485                 490                 495

Glu Glu Glu Glu Ile Arg Ile Leu Cys His Glu Lys Gln Pro Arg Ser
            500                 505                 510

Leu Gly Asp Lys Lys Leu Lys Lys Tyr Ser Thr Arg Leu Ile His Leu
        515                 520                 525

Ala Asn Lys Gln Gln Leu Glu Ser Leu Asp Ala Ile Arg Cys Leu Pro
    530                 535                 540

His Val Thr Arg Gly Ser Leu Val Lys Arg Asn Arg Gly Arg Asp Trp
545                 550                 555                 560

Asn Phe Asp Asp Leu Tyr Gly Ser Gly Ser Tyr Ser Val Pro Ser Lys
                565                 570                 575

Ala Lys Ile Leu Val Ser Ile Pro Arg Lys Thr Asn Ile
            580                 585

<210> SEQ ID NO 4
<211> LENGTH: 528
<212> TYPE: PRT
<213> ORGANISM: Acyrthosiphon pisum

<400> SEQUENCE: 4

Met Ala Ile Lys Ile Ile Ile Gly Ser Gly Val Gly Gly Thr Ala
1               5                   10                  15

Ala Ala Ala Arg Leu Ser Lys Lys Gly Phe Gln Val Glu Val Tyr Glu
                20                  25                  30

Lys Asn Ser Tyr Asn Gly Gly Arg Cys Ser Ile Ile Arg His Asn Gly
            35                  40                  45

His Arg Phe Asp Gln Gly Pro Ser Leu Tyr Leu Met Pro Lys Ile Phe
        50                  55                  60

Glu Glu Thr Phe Lys Asp Leu Gly Glu Asp Ile Lys Asp His Ile Glu
65                  70                  75                  80

Ile Leu Gln Cys Lys Ile Asn Tyr Tyr Ile Asn Phe His Asp Gly Gln
                85                  90                  95

Gln Phe Gln His Ser Cys Asn Leu Ser Lys Leu Gln Arg Ser Leu Glu
            100                 105                 110

Asn Phe Glu Gly Glu Gly Glu Thr Leu Leu Arg Phe Phe Asp Phe
        115                 120                 125

Leu Lys Glu Thr His Val His Tyr Arg Lys Ser Ile Glu Leu Ala Met
    130                 135                 140

Arg Thr Asp Phe Gln Asn Trp Tyr Asp Phe Phe Asn Ile Lys His Ile
145                 150                 155                 160

Pro Thr Leu Leu Asn Leu His Leu His Ser Ser Val Tyr Thr Arg Ala
                165                 170                 175

Cys Lys Tyr Phe Lys Ser Asp Tyr Met Arg Lys Ala Phe Thr Phe Gln
            180                 185                 190

Thr Met Tyr Met Gly Met Ser Pro Tyr Asp Gly Leu Ala Pro Tyr Asn
        195                 200                 205

Leu Leu Gln Tyr Thr Glu Ile Ala Glu Gly Ile Trp Tyr Pro Lys Gly
    210                 215                 220

Gly Phe His Ser Val Leu Glu Ser Leu Glu Lys Ile Ala Val Lys His
225                 230                 235                 240

Gly Ala Lys Phe Asn Tyr Asn Ser Asp Val Gln Glu Ile Ile Thr Asp 245                 250                 255
Glu Asn Gly Val Ala Lys Gly Ile Lys Leu Gln Asn Gly Asn Val Ile
            260                 265                 270

Asn Ser Asp Ile Val Ile Cys Asn Ala Asp Ala Val Tyr Ala Tyr Asn
        275                 280                 285

Lys Leu Leu Pro Lys Thr Ser Tyr Ala Glu Lys Leu Gly Lys Lys Lys
    290                 295                 300

Leu Thr Ser Ser Ile Ser Phe Tyr Trp Ser Ile Asn Gln Val Ile
305                 310                 315                 320

Pro Gln Met Ser Val His Asn Ile Phe Leu Ser Glu Gln Tyr Lys Pro
                325                 330                 335

Ser Phe Asp Gln Ile Phe Glu Asp His Ser Leu Pro Asp Glu Pro Ser
            340                 345                 350

Phe Tyr Val Asn Val Pro Ser His Ile Asp Pro Thr Ala Ala Pro Glu
        355                 360                 365

Gly Lys Asp Thr Phe Val Ile Leu Val Pro Val Gly His Ile Ser Asp
    370                 375                 380

Arg Thr Asp Ile Asp Phe Asp Asp Leu Val Lys Arg Ala Arg Glu His
385                 390                 395                 400

Val Ile Asn Ser Ile Glu Lys Arg Leu Lys Ile Ser Asn Phe Arg Ser
                405                 410                 415

Met Ile Glu His Glu Met Val Asn Asp Pro Arg Thr Trp Gln Ser Glu
            420                 425                 430

Phe Asn Leu Trp Lys Gly Ser Val Leu Gly Leu Ser His Ser Phe Phe
        435                 440                 445

Gln Val Ala Tyr Phe Arg Pro Ser Leu Lys Cys Lys Ile Phe Glu Asn
    450                 455                 460

Leu Tyr Phe Val Gly Ala Ser Val Gln Pro Gly Thr Gly Val Pro Val
465                 470                 475                 480

Val Leu Cys Gly Ala Lys Leu Leu Glu Lys Gln Leu Cys Ala Arg Phe
                485                 490                 495

Leu Glu Gly Lys Val Glu Met Asn Thr Trp Ser Lys Tyr Val Ser Phe
            500                 505                 510

Leu Ile Gly Leu Leu Val Leu Leu Ile Phe Trp Phe Phe Arg Phe
        515                 520                 525

<210> SEQ ID NO 5
<211> LENGTH: 528
<212> TYPE: PRT
<213> ORGANISM: Acyrthosiphon pisum

<400> SEQUENCE: 5

Met Val Val Lys Ile Ile Ile Gly Ala Gly Val Gly Gly Thr Ala
1               5                   10                  15

Ala Ala Ala Arg Leu Ser Lys Arg Gly Phe Gln Val Glu Val Phe Glu
            20                  25                  30

Lys Asn Ala Tyr Asn Gly Gly Arg Cys Ser Leu Ile Gln His Lys Gly
        35                  40                  45

His Arg Phe Asp Gln Gly Pro Ser Leu Tyr Leu Met Pro Lys Ile Phe
    50                  55                  60

Glu Glu Thr Phe Glu Asp Leu Gly Glu Asp Ile Lys Asn His Ile Asp
65                  70                  75                  80

Leu Leu Lys Cys Pro Ser Asn Tyr Ser Val His Phe His Asp Gly Glu
                85                  90                  95

```
Thr Phe Glu Leu Thr Thr Asp Ile Ser Lys Leu Ser Arg Ser Leu Glu
            100                 105                 110
Lys Tyr Glu Gly Ser Gly Glu Ser Thr Leu Ile Asn Phe Leu Ser Tyr
        115                 120                 125
Leu Lys Glu Thr His Val His Tyr Gln Arg Ser Val Lys Val Ala Leu
    130                 135                 140
Lys Thr Asp Phe Gln His Trp Tyr Asp Phe Phe Asn Pro Lys His Ile
145                 150                 155                 160
Pro Asp Val Ile Gln Leu His Leu Leu Asp Thr Val Tyr Asn Arg Val
                165                 170                 175
Cys Lys Tyr Phe Lys Ser Asp Tyr Met Arg Lys Ala Phe Ser Phe Gln
            180                 185                 190
Thr Met Tyr Leu Gly Met Ser Pro Tyr Asp Gly Leu Ala Pro Tyr Ser
        195                 200                 205
Leu Leu Gln Tyr Thr Glu Ile Ala Glu Gly Ile Trp Tyr Pro Lys Gly
    210                 215                 220
Gly Phe Asn Lys Val Leu Gln Ser Leu Glu Gln Ile Ala Val Gln Tyr
225                 230                 235                 240
Gly Ala Lys Phe Asn Tyr Lys Thr Asn Val Gln Glu Ile Ile Val Asp
                245                 250                 255
Asp Lys Gly Val Ala Lys Gly Ile Lys Met Val Asn Gly Asp Val Val
            260                 265                 270
Asn Ser Asp Ile Val Ile Cys Asn Ala Asp Leu Val Tyr Ala Tyr Asn
        275                 280                 285
Lys Leu Leu Pro Lys Thr Ser Tyr Ala Asn Lys Leu Gly Lys Lys Glu
    290                 295                 300
Leu Thr Ser Ser Ser Ile Ser Phe Tyr Trp Ser Met Lys Thr Ile Val
305                 310                 315                 320
Pro Gln Leu Lys Val His Asn Ile Phe Leu Ala Glu Lys Tyr Lys Glu
                325                 330                 335
Ser Phe Asp Gln Ile Phe Lys Asp His Thr Leu Pro Asp Glu Pro Ser
            340                 345                 350
Phe Tyr Val Asn Val Pro Ser Arg Ile Asp Pro Ser Ala Ala Pro Glu
        355                 360                 365
Gly Lys Asp Thr Ile Val Val Leu Val Pro Val Gly His Ile Ser Asn
    370                 375                 380
Val Pro Asn Ile Asp Phe Asp Lys Leu Val Glu Arg Ala Arg Glu Gln
385                 390                 395                 400
Val Ile Asp Thr Ile Glu Lys Arg Leu Lys Ile Ser Asn Phe Arg Ser
                405                 410                 415
Met Ile Asp His Glu Ile Val Asn Asp Pro Arg Thr Trp Gln Asn Glu
            420                 425                 430
Phe Asn Leu Trp Lys Gly Ser Ile Gly Leu Ser His Ser Leu Phe
        435                 440                 445
Gln Val Leu Trp Phe Arg Pro Ser Leu Lys Cys Lys Ile Phe Glu Asn
    450                 455                 460
Leu Tyr Phe Val Gly Ala Ser Ala Gln Pro Gly Thr Gly Val Pro Ile
465                 470                 475                 480
Val Leu Cys Gly Ala Lys Met Leu Glu Lys Gln Leu Cys Asp Arg Phe
                485                 490                 495
Leu Asp Ser Lys Val Glu Ile Ser Ile Trp Ser Lys Cys Val Ser Phe
            500                 505                 510
Leu Ile Gly Leu Leu Ala Leu Leu Ile Phe Trp Phe Phe Phe Arg Phe
```

515         520         525

<210> SEQ ID NO 6
<211> LENGTH: 526
<212> TYPE: PRT
<213> ORGANISM: Acyrthosiphon pisum

<400> SEQUENCE: 6

Met Val Val Lys Ile Ile Ile Gly Ala Gly Val Gly Thr Ala
1               5                   10                  15

Ala Ala Ala Arg Leu Ser Lys Lys Gly Phe Gln Val Glu Ile Tyr Glu
            20                  25                  30

Lys Asn Ala Tyr Asn Gly Gly Arg Cys Ser Leu Ile Tyr Gln Asn Gly
        35                  40                  45

His Arg Phe Asp Gln Gly Pro Ser Leu Tyr Leu Met Pro Lys Ile Phe
    50                  55                  60

Glu Glu Ile Phe Glu Asp Leu Gly Glu Asp Ile Lys Asn His Ile Asp
65                  70                  75                  80

Leu Leu Lys Cys Pro Ser Asn Tyr Ser Val His Phe His Asp Gly Glu
                85                  90                  95

Thr Phe Glu Leu Thr Thr Asp Ile Ser Lys Leu Ser Arg Ser Leu Glu
            100                 105                 110

Lys Tyr Glu Gly Tyr Gly Glu Ser Thr Leu Ile Asn Phe Leu Arg Tyr
        115                 120                 125

Leu Lys Glu Thr His Val His Tyr Gln Arg Ser Val Lys Val Ala Leu
    130                 135                 140

Lys Thr Asp Phe Gln His Trp Tyr Asp Phe Phe Asn Pro Lys Phe Leu
145                 150                 155                 160

Pro Asp Val Ile Gln Leu His Leu Leu Asp Thr Val Tyr Asn Arg Val
                165                 170                 175

Cys Lys Tyr Phe Lys Ser Asp Tyr Met Arg Lys Ala Phe Ser Phe Gln
            180                 185                 190

Thr Met Tyr Leu Gly Met Ser Pro Tyr Asp Gly Leu Ala Ala Tyr Ser
        195                 200                 205

Leu Leu Gln Tyr Thr Glu Ile Ala Glu Gly Ile Trp Tyr Pro Lys Gly
    210                 215                 220

Gly Phe His Lys Val Leu Glu Ser Leu Glu Asn Ile Ala Val Gln His
225                 230                 235                 240

Gly Ala Lys Phe Asn Tyr Asn Ala Asp Val Gln Glu Ile Ile Val Asp
                245                 250                 255

Asp Lys Gly Val Ala Lys Gly Ile Lys Met Val Asn Gly Asp Val Val
            260                 265                 270

Asn Ser Asp Ile Val Ile Cys Asn Ala Asp Leu Val Tyr Ala Tyr Asn
        275                 280                 285

Lys Leu Leu Pro Lys Thr Ser Tyr Ala Asp Lys Leu Gly Lys Lys Glu
    290                 295                 300

Leu Thr Ser Ser Ser Ile Ser Phe Tyr Trp Ser Met Lys Thr Ile Val
305                 310                 315                 320

Ser Gln Leu Lys Val His Asn Ile Phe Leu Ala Glu Lys Tyr Lys Glu
                325                 330                 335

Ser Phe Asp Gln Ile Phe Lys Asp His Thr Leu Pro Asp Glu Pro Ser
            340                 345                 350

Phe Tyr Val Asn Val Pro Ser Arg Ile Asp Pro Thr Ala Ala Pro Glu
        355                 360                 365

```
Gly Lys Asp Thr Ile Val Val Leu Val Pro Val Gly His Ile Ser Asn
    370                 375                 380

Val Pro Asn Ile Asp Phe Asp Gln His Val Lys Thr Ala Arg Glu His
385                 390                 395                 400

Val Ile Asp Thr Ile Glu Lys Arg Leu Lys Ile Ser Asn Phe Arg Ser
                405                 410                 415

Met Ile Asp His Glu Ile Val Asn Asp Pro Arg Thr Trp Gln Asn Asn
            420                 425                 430

Phe Asn Leu Trp Lys Gly Ser Ile Gly Leu Ser His Ser Leu Phe
        435                 440                 445

Gln Val Leu Trp Phe Arg Pro Ser Met Lys Cys Lys Ile Phe Glu Asn
450                 455                 460

Leu Tyr Phe Val Gly Ala Ser Val Gln Pro Gly Thr Gly Val Pro Ile
465                 470                 475                 480

Val Leu Cys Gly Thr Lys Leu Leu Glu Lys Gln Leu Cys Asp Arg Phe
                485                 490                 495

Leu Asp Ser Lys Val Thr Lys Ser Ser Trp Ser Met Cys Val Ser Phe
            500                 505                 510

Leu Ile Gly Ile Ile Val Leu Leu Ile Phe Cys Thr Leu Phe
        515                 520                 525

<210> SEQ ID NO 7
<211> LENGTH: 510
<212> TYPE: PRT
<213> ORGANISM: Acyrthosiphon pisum

<400> SEQUENCE: 7

Met Val Val Lys Ile Ile Ile Gly Ser Gly Val Gly Gly Thr Ala
1               5                   10                  15

Val Ala Ala Arg Leu Ser Lys Lys Gly Phe Gln Val Glu Ile Tyr Glu
                20                  25                  30

Lys Asn Ser Tyr Asn Gly Gly Arg Cys Ser Leu Ile Tyr Gln Asn Gly
            35                  40                  45

His Arg Phe Asp Gln Gly Pro Ser Leu Tyr Leu Met Pro Lys Ile Phe
        50                  55                  60

Glu Glu Thr Phe Glu Asp Leu Gly Asp Ile Lys Asn His Ile Glu
65                  70                  75                  80

Leu Leu Lys Cys Pro Thr Asn Tyr Ser Val His Phe His Asp Gly Glu
                85                  90                  95

Thr Phe Glu Leu Thr Thr Asp Ile Ser Lys Leu Ser Arg Ser Leu Glu
            100                 105                 110

Lys Tyr Glu Gly Ser Gly Glu Ser Thr Leu Ile Asn Phe Leu Asn Tyr
        115                 120                 125

Leu Lys Leu Thr His Leu Tyr Tyr Arg Lys Ser Val Asn Val Ile Gln
    130                 135                 140

Leu His Leu Leu Asp Thr Val Tyr Asn Lys Val Ser Lys Tyr Phe Lys
145                 150                 155                 160

Ser Asp Tyr Met Arg Lys Ala Phe Ser Phe Gln Thr Met Tyr Leu Gly
                165                 170                 175

Met Ser Pro Tyr Asp Gly Leu Ala Leu Tyr Ser Leu Gln Tyr Thr
            180                 185                 190

Glu Ile Ala Glu Gly Ile Trp Tyr Pro Lys Gly Gly Tyr His Lys Val
        195                 200                 205

Leu Glu Ile Leu Glu Lys Ile Ala Val Gln His Gly Ala Lys Phe Asn
    210                 215                 220
```

-continued

Tyr Asn Ala Asp Val Gln Glu Ile Ile Ile Asp Asp Lys Gly Val Ala
225                 230                 235                 240

Lys Gly Ile Lys Leu Val Asn Gly Asp Val Asn Ser Asp Ile Val
            245                 250                 255

Ile Cys Asn Ala Asp Leu Thr Tyr Ala Tyr Asn Lys Leu Leu Pro Lys
            260                 265                 270

Thr Ser Tyr Ala Glu Lys Leu Asp Lys Lys Glu His Thr Ser Ser Ser
        275                 280                 285

Ile Ser Phe Tyr Trp Ser Met Asn Thr Ile Val Ser Gln Leu Asn Val
        290                 295                 300

His Asn Ile Phe Leu Ala Glu Lys Tyr Lys Ser Phe Asp Gln Ile
305                 310                 315                 320

Phe Lys Asp His Thr Leu Pro Asp Asp Pro Ser Phe Tyr Val Asn Val
                325                 330                 335

Pro Ser Arg Ile Asp Pro Thr Ala Ala Pro Glu Gly Lys Asp Ser Ile
            340                 345                 350

Val Val Leu Val Pro Val Gly His Leu Ser Asn Glu Pro Asn Ile Asp
        355                 360                 365

Phe Asp Lys Leu Val Asn Lys Ala Arg Glu Gln Val Ile Asp Thr Ile
370                 375                 380

Glu Lys Arg Leu Lys Ile Ser Asn Phe Arg Ser Met Ile Asp His Glu
385                 390                 395                 400

Lys Val Asn Asp Pro Arg Thr Trp Arg Asn Glu Phe Asn Leu Trp Lys
                405                 410                 415

Gly Ser Ile Leu Gly Leu Ser His Thr Phe Leu Gln Val Val Trp Phe
            420                 425                 430

Arg Pro Ser Leu Lys Cys Asn Ile Phe Lys Asn Leu Tyr Phe Val Gly
        435                 440                 445

Ala Ser Ala His Pro Gly Thr Gly Val Pro Val Val Leu Cys Gly Ala
        450                 455                 460

Lys Leu Leu Glu Asn Gln Leu Cys Asp Arg Phe Leu Lys Ser Lys Ala
465                 470                 475                 480

Lys Leu Ser Leu Trp Ser Lys Cys Val Ser Phe Leu Ile Ser Leu Leu
                485                 490                 495

Thr Leu Leu Phe Leu Trp Ile Ser Leu Phe Phe Asn Lys Thr
            500                 505                 510

<210> SEQ ID NO 8
<211> LENGTH: 315
<212> TYPE: PRT
<213> ORGANISM: Mus musculus

<400> SEQUENCE: 8

Met Ser Thr Gln Glu Pro Gln Lys Ser Leu Leu Gly Ser Leu Asn Ser
1               5                   10                  15

Asn Ala Thr Ser His Leu Gly Leu Ala Thr Asn Gln Ser Glu Pro Trp
            20                  25                  30

Cys Leu Tyr Val Ser Ile Pro Asp Gly Leu Phe Leu Ser Leu Gly Leu
        35                  40                  45

Val Ser Leu Val Glu Asn Leu Val Val Ile Ala Ile Thr Lys Asn
    50                  55                  60

Arg Asn Leu His Ser Pro Met Tyr Tyr Phe Ile Cys Cys Leu Ala Leu
65                  70                  75                  80

Ser Asp Leu Met Val Ser Val Ser Ile Val Leu Glu Thr Thr Ile Ile

```
                    85                  90                  95
Leu Leu Leu Glu Ala Gly Ile Leu Val Ala Arg Val Ala Leu Val Gln
                100                 105                 110

Gln Leu Asp Asn Leu Ile Asp Val Leu Ile Cys Gly Ser Met Val Ser
            115                 120                 125

Ser Leu Cys Phe Leu Gly Ile Ala Ile Asp Arg Tyr Ile Ser Ile
        130                 135                 140

Phe Tyr Ala Leu Arg Tyr His Ser Ile Val Thr Leu Pro Arg Ala Arg
145                 150                 155                 160

Arg Ala Val Val Gly Ile Trp Met Val Ser Ile Val Ser Ser Thr Leu
                165                 170                 175

Phe Ile Thr Tyr Tyr Lys His Thr Ala Val Leu Leu Cys Leu Val Thr
            180                 185                 190

Phe Phe Leu Ala Met Leu Ala Leu Met Ala Ile Leu Tyr Ala His Met
        195                 200                 205

Phe Thr Arg Ala Cys Gln His Ala Gln Gly Ile Ala Gln Leu His Lys
        210                 215                 220

Arg Arg Arg Ser Ile Arg Gln Gly Phe Cys Leu Lys Gly Ala Ala Thr
225                 230                 235                 240

Leu Thr Ile Leu Leu Gly Ile Phe Phe Leu Cys Trp Gly Pro Phe Phe
                245                 250                 255

Leu His Leu Leu Leu Ile Val Leu Cys Pro Gln His Pro Thr Cys Ser
            260                 265                 270

Cys Ile Phe Lys Asn Phe Asn Leu Phe Leu Leu Leu Ile Val Leu Ser
        275                 280                 285

Ser Thr Val Asp Pro Leu Ile Tyr Ala Phe Arg Ser Gln Glu Leu Arg
        290                 295                 300

Met Thr Leu Lys Glu Val Leu Leu Cys Ser Trp
305                 310                 315

<210> SEQ ID NO 9
<211> LENGTH: 13
<212> TYPE: PRT
<213> ORGANISM: Artificial sequence
<220> FEATURE:
<223> OTHER INFORMATION: Alpha melanocyte stimulating hormone

<400> SEQUENCE: 9

Ser Tyr Ser Met Glu His Phe Arg Trp Gly Lys Pro Val
1               5                   10

<210> SEQ ID NO 10
<211> LENGTH: 22
<212> TYPE: PRT
<213> ORGANISM: Homo sapiens

<400> SEQUENCE: 10

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 11
<211> LENGTH: 18
<212> TYPE: PRT
<213> ORGANISM: Sus scrofa

<400> SEQUENCE: 11
```

```
Asp Glu Gly Pro Tyr Lys Met Glu His Phe Arg Trp Gly Ser Pro Pro
1               5                   10                  15

Lys Asp

<210> SEQ ID NO 12
<211> LENGTH: 12
<212> TYPE: PRT
<213> ORGANISM: Artificial sequence
<220> FEATURE:
<223> OTHER INFORMATION: gamma melanocyte stimulating hormone

<400> SEQUENCE: 12

Tyr Val Met Gly His Phe Arg Trp Asp Arg Phe Gly
1               5                   10

<210> SEQ ID NO 13
<211> LENGTH: 67
<212> TYPE: PRT
<213> ORGANISM: Mus musculus

<400> SEQUENCE: 13

Met Lys Leu Leu Leu Thr Leu Ala Ala Leu Leu Val Ser Gln
1               5                   10                  15

Leu Thr Pro Gly Asp Ala Gln Lys Cys Trp Asn Leu His Gly Lys Cys
                20                  25                  30

Arg His Arg Cys Ser Arg Lys Glu Ser Val Tyr Val Tyr Cys Thr Asn
            35                  40                  45

Gly Lys Met Cys Cys Val Lys Pro Lys Tyr Gln Pro Lys Pro Lys Pro
    50                  55                  60

Trp Met Phe
65

<210> SEQ ID NO 14
<211> LENGTH: 131
<212> TYPE: PRT
<213> ORGANISM: Mus musculus

<400> SEQUENCE: 14

Met Asp Val Thr Arg Leu Leu Leu Ala Thr Leu Val Gly Phe Leu Cys
1               5                   10                  15

Phe Phe Thr Val His Ser His Leu Ala Leu Glu Glu Thr Leu Gly Asp
                20                  25                  30

Asp Arg Ser Leu Arg Ser Asn Ser Ser Met Asn Ser Leu Asp Phe Ser
            35                  40                  45

Ser Val Ser Ile Val Ala Leu Asn Lys Lys Ser Lys Lys Ile Ser Arg
    50                  55                  60

Lys Glu Ala Glu Lys Arg Lys Arg Ser Ser Lys Lys Lys Ala Ser Met
65                  70                  75                  80

Lys Lys Val Ala Arg Pro Pro Pro Pro Ser Pro Cys Val Ala Thr Arg
                85                  90                  95

Asp Ser Cys Lys Pro Pro Ala Pro Ala Cys Cys Asp Pro Cys Ala Ser
            100                 105                 110

Cys Gln Cys Arg Phe Phe Gly Ser Ala Cys Thr Cys Arg Val Leu Asn
    115                 120                 125

Pro Asn Cys
    130

<210> SEQ ID NO 15
<211> LENGTH: 533
```

<212> TYPE: PRT
<213> ORGANISM: Mus musculus

<400> SEQUENCE: 15

```
Met Phe Leu Ala Val Leu Tyr Cys Leu Leu Trp Ser Phe Gln Ile Ser
1               5                   10                  15

Asp Gly His Phe Pro Arg Ala Cys Ser Ser Lys Asn Leu Leu Ala
            20                  25                  30

Lys Glu Cys Cys Pro Pro Trp Met Gly Asp Gly Ser Pro Cys Gly Gln
        35                  40                  45

Leu Ser Gly Arg Gly Ser Cys Gln Asp Ile Leu Leu Ser Ser Ala Pro
    50                  55                  60

Ser Gly Pro Gln Phe Pro Phe Lys Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Gly Gly Pro Asn Cys
            100                 105                 110

Thr Glu Lys Arg Val Leu Ile Arg Arg Asn Ile Phe Asp Leu Ser Val
        115                 120                 125

Ser Glu Lys Asn Lys Phe Phe Ser Tyr Leu Thr Leu Ala Lys His Thr
    130                 135                 140

Ile Ser Ser Val Tyr Val Ile Pro Thr Gly Thr Tyr Gly Gln Met Asn
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Arg Asp Thr Leu Leu Gly Gly Ser
            180                 185                 190

Glu Ile Trp Arg Asp Ile Asp Phe Ala His Glu Ala Pro Gly Phe Leu
        195                 200                 205

Pro Trp His Arg Leu Phe Leu Leu Leu Trp Glu Gln Glu Ile Arg Glu
    210                 215                 220

Leu Thr Gly Asp Glu Asn Phe Thr Val Pro Tyr Trp Asp Trp Arg Asp
225                 230                 235                 240

Ala Glu Asn Cys Asp Ile Cys Thr Asp Glu Tyr Leu Gly Gly Arg His
                245                 250                 255

Pro Glu Asn Pro Asn Leu Leu Ser Pro Ala Ser Phe Phe Ser Ser Trp
            260                 265                 270

Gln Ile Ile Cys Ser Arg Ser Glu Glu Tyr Asn Ser His Gln Val Leu
        275                 280                 285

Cys Asp Gly Thr Pro Glu Gly Pro Leu Leu Arg Asn Pro Gly Asn His
    290                 295                 300

Asp Lys Ala Lys Thr Pro Arg Leu Pro Ser Ala Asp Val Glu Phe
305                 310                 315                 320

Cys Leu Ser Leu Thr Gln Tyr Glu Ser Gly Ser Met Asp Arg Thr Ala
                325                 330                 335

Asn Phe Ser Phe Arg Asn Thr Leu Glu Gly Phe Ala Ser Pro Leu Thr
            340                 345                 350

Gly Ile Ala Asp Pro Ser Gln Ser Ser Met His Asn Ala Leu His Ile
        355                 360                 365

Phe Met Asn Gly Thr Met Ser Gln Val Gln Gly Ser Ala Asn Asp Pro
    370                 375                 380

Ile Phe Leu Leu His His Ala Phe Val Asp Ser Ile Phe Glu Gln Trp
385                 390                 395                 400
```

```
Leu Arg Arg His Arg Pro Leu Leu Glu Val Tyr Pro Glu Ala Asn Ala
            405                 410                 415

Pro Ile Gly His Asn Arg Asp Ser Tyr Met Val Pro Phe Ile Pro Leu
            420                 425                 430

Tyr Arg Asn Gly Asp Phe Phe Ile Thr Ser Lys Asp Leu Gly Tyr Asp
            435                 440                 445

Tyr Ser Tyr Leu Gln Glu Ser Asp Pro Gly Phe Tyr Arg Asn Tyr Ile
            450                 455                 460

Glu Pro Tyr Leu Glu Gln Ala Ser Arg Ile Trp Pro Trp Leu Leu Gly
465                 470                 475                 480

Ala Ala Leu Val Gly Ala Val Ile Ala Ala Leu Ser Gly Leu Ser
            485                 490                 495

Ser Arg Leu Cys Leu Gln Lys Lys Lys Lys Lys Gln Pro Gln Glu
            500                 505                 510

Glu Arg Gln Pro Leu Leu Met Asp Lys Asp Asp Tyr His Ser Leu Leu
            515                 520                 525

Tyr Gln Ser His Leu
    530
```

```
<210> SEQ ID NO 16
<211> LENGTH: 833
<212> TYPE: PRT
<213> ORGANISM: Mus musculus

<400> SEQUENCE: 16

Met Arg Leu Glu Asn Lys Asp Ile Arg Leu Ala Ser Ala Val Leu Glu
1               5                   10                  15

Val Glu Leu His Gln Thr Ser Ala Leu Ser Val Pro Thr Cys Pro Asp
            20                  25                  30

Pro Gly Arg Leu Leu Thr Val Lys Pro Ala Thr Ser Asn Tyr Lys Leu
            35                  40                  45

Gly Gln Ala Asp Pro Cys Ile Pro Tyr Ala Gly Glu Ala Ala Gly Lys
        50                  55                  60

Ser Val Cys Val Pro Glu His Thr Glu Phe Gly Ser Phe Leu Val Lys
65                  70                  75                  80

Gly Ser Ser Ser Leu Lys Asp Leu Ser Phe Lys Glu Asp Thr Pro Leu
                85                  90                  95

Leu Trp Asn Ser Ser Gln Lys Lys Arg Ser Gln Leu Met Pro Val His
            100                 105                 110

His Pro Glu Phe Ile Ala Thr Glu Gly Ser Trp Glu Asn Gly Leu Thr
        115                 120                 125

Ala Trp Glu Gln Lys Cys Met Leu Gly Lys Glu Val Ala Asp Leu Ser
    130                 135                 140

Ala Leu Ala Ser Ser Glu Lys Arg Asp Leu Ala Gly Ser Val His Leu
145                 150                 155                 160

Arg Ala Gln Val Ser Lys Leu Gly Cys Cys Val Arg Trp Ile Lys Ile
                165                 170                 175

Thr Gly Leu Phe Val Phe Val Val Leu Cys Ser Ile Leu Phe Ser Leu
            180                 185                 190

Tyr Pro Asp Gln Gly Lys Phe Trp Gln Leu Leu Ala Val Ser Pro Leu
        195                 200                 205

Glu Asn Tyr Ser Val Asn Leu Ser Gly His Ala Asp Ser Met Ile Leu
    210                 215                 220

Gln Leu Asp Leu Ala Gly Ala Leu Met Ala Gly Gly Pro Ser Gly Ser
```

-continued

```
            225                 230                 235                 240
Gly Lys Glu Glu His Val Val Val Val Thr Gln Thr Asp Ala Ala
                    245                 250                 255
Gly Asn Arg Arg Arg Pro Gln Gln Leu Thr Tyr Asn Trp Thr Val
                    260                 265                 270
Leu Leu Asn Pro Arg Ser Glu His Val Val Ser Arg Thr Phe Glu
                    275                 280                 285
Ile Val Ser Arg Glu Ala Val Ser Ile Ser Ile Gln Ala Ser Leu Gln
                    290                 295                 300
Gln Thr Arg Leu Val Pro Leu Leu Ala His Gln Phe Leu Gly Ala
305                 310                 315                 320
Ser Val Glu Ala Gln Val Ala Ser Ala Val Ala Ile Leu Ala Gly Val
                    325                 330                 335
Tyr Thr Leu Ile Ile Phe Glu Ile Val His Arg Thr Leu Ala Ala Met
                    340                 345                 350
Leu Gly Ala Leu Ala Ala Leu Ala Ala Leu Ala Val Val Gly Asp Arg
                    355                 360                 365
Pro Ser Leu Thr His Val Val Glu Trp Ile Asp Phe Glu Thr Leu Ala
                    370                 375                 380
Leu Leu Phe Gly Met Met Ile Leu Val Ala Val Phe Ser Glu Thr Gly
385                 390                 395                 400
Phe Phe Asp Tyr Cys Ala Val Lys Ala Tyr Gln Leu Ser Arg Gly Arg
                    405                 410                 415
Val Trp Ala Met Ile Phe Met Leu Cys Leu Met Ala Ala Ile Leu Ser
                    420                 425                 430
Ala Phe Leu Asp Asn Val Thr Thr Met Leu Leu Phe Thr Pro Val Thr
                    435                 440                 445
Ile Arg Leu Cys Glu Val Leu Asn Leu Asp Pro Arg Gln Val Leu Ile
                    450                 455                 460
Ala Glu Val Ile Phe Thr Asn Ile Gly Gly Ala Ala Thr Ala Ile Gly
465                 470                 475                 480
Asp Pro Pro Asn Val Ile Ile Val Ser Asn Gln Glu Leu Arg Lys Met
                    485                 490                 495
Gly Leu Asp Phe Ala Gly Phe Thr Ala His Met Phe Leu Gly Ile Cys
                    500                 505                 510
Leu Val Leu Leu Val Ser Phe Pro Leu Leu Arg Leu Leu Tyr Trp Asn
                    515                 520                 525
Lys Lys Leu Tyr Asn Lys Glu Pro Ser Glu Ile Val Glu Leu Lys His
                    530                 535                 540
Glu Ile His Val Trp Arg Leu Thr Ala Gln Arg Ile Ser Pro Ala Ser
545                 550                 555                 560
Arg Glu Glu Thr Ala Val Arg Gly Leu Leu Glu Lys Val Leu Ala
                    565                 570                 575
Leu Glu His Leu Leu Ala Gln Arg Leu His Thr Phe His Arg Gln Ile
                    580                 585                 590
Ser Gln Glu Asp Lys Asn Trp Glu Thr Asn Ile Gln Glu Leu Gln Arg
                    595                 600                 605
Lys His Arg Ile Ser Asp Arg Ser Leu Leu Val Lys Cys Leu Thr Val
                    610                 615                 620
Leu Gly Phe Val Ile Ser Met Phe Phe Leu Asn Ser Phe Val Pro Gly
625                 630                 635                 640
Ile His Leu Asp Leu Gly Trp Ile Ala Ile Leu Gly Ala Ile Trp Leu
                    645                 650                 655
```

-continued

```
Leu Ile Leu Ala Asp Ile His Asp Phe Glu Ile Leu His Arg Val
            660                 665                 670
Glu Trp Ala Thr Leu Leu Phe Phe Ala Ala Leu Phe Val Leu Met Glu
        675                 680                 685
Ala Leu Thr His Leu His Leu Val Glu Tyr Val Gly Glu Gln Thr Ala
    690                 695                 700
Leu Leu Ile Lys Met Val Pro Glu Asp Gln Arg Phe Ala Ala Ala Ile
705                 710                 715                 720
Val Leu Ile Val Trp Val Ser Ala Leu Ala Ser Ser Leu Ile Asp Asn
                725                 730                 735
Ile Pro Phe Thr Ala Thr Met Ile Pro Val Leu Leu Asn Leu Ser Gln
            740                 745                 750
Asp Pro Glu Ile Ser Leu Pro Ala Leu Pro Leu Met Tyr Ala Leu Ala
        755                 760                 765
Leu Gly Ala Cys Leu Gly Gly Asn Gly Thr Leu Ile Gly Ala Ser Thr
    770                 775                 780
Asn Val Val Cys Ala Gly Ile Ala Glu Lys His Gly Tyr Gly Phe Ser
785                 790                 795                 800
Phe Met Glu Phe Phe Arg Leu Gly Phe Pro Val Met Leu Met Ser Cys
                805                 810                 815
Thr Ile Gly Met Cys Tyr Leu Leu Ile Ala His Ile Val Val Gly Trp
            820                 825                 830
Asn

<210> SEQ ID NO 17
<211> LENGTH: 621
<212> TYPE: PRT
<213> ORGANISM: Mus musculus

<400> SEQUENCE: 17

Met Ala Glu Lys Leu Pro Thr Glu Phe Asp Val Val Ile Ile Gly Thr
1               5                   10                  15
Gly Leu Pro Glu Ser Ile Leu Ala Ala Ala Cys Ser Arg Ser Gly Gln
            20                  25                  30
Arg Val Leu His Val Asp Ser Arg Ser Tyr Tyr Gly Gly Asn Trp Ala
        35                  40                  45
Ser Phe Ser Phe Thr Gly Leu Gln Ser Trp Leu Lys Asp Tyr Gln Gln
    50                  55                  60
Asn His Asp Ser Glu Glu Gly Val Thr Ala Thr Trp Gln Asp Leu Ile
65                  70                  75                  80
His Glu Thr Glu Glu Ala Ile Ser Leu Arg Lys Lys Asp Glu Thr Ile
                85                  90                  95
Gln His Thr Glu Val Phe Cys Tyr Ala Ser Gln Asp Val Glu Asp Ser
            100                 105                 110
Val Gln Asp Thr Glu Thr Leu Gln Arg Ser Ser Pro Leu Glu Ala Ser
        115                 120                 125
Ala Thr Pro Ala Asp Ser Leu Asp Ser Ala Ser Leu Pro Lys Glu Arg
    130                 135                 140
Gln Ser Ala Tyr Ser Thr Ser Tyr Glu Val Pro Ser Arg His Thr Glu
145                 150                 155                 160
Glu Ser Asp Arg Glu Leu Ser Leu Pro Ser Ala Asn Val Glu Asp Ser
                165                 170                 175
Leu Glu Lys Glu Lys Tyr Cys Gly Asp Lys Thr Asp Met His Thr Val
            180                 185                 190
```

Ser Gly Glu Asp Lys Gly Glu His Lys Leu Val Val Gln Asp Ser Ile
                195                 200                 205

Glu Gln Pro Lys Arg Asn Arg Ile Thr Tyr Ser Gln Met Val Lys Glu
            210                 215                 220

Ser Arg Arg Phe Asn Ile Asp Leu Val Ser Lys Pro Leu Tyr Ser Gln
225                 230                 235                 240

Gly Ser Leu Ile Asp Leu Leu Ile Lys Ser Asn Val Ser Arg Tyr Ala
                245                 250                 255

Glu Phe Lys Asn Val Thr Arg Ile Leu Ala Phe Trp Glu Gly Lys Val
            260                 265                 270

Glu Gln Val Pro Cys Ser Arg Ala Asp Val Phe Asn Ser Lys Glu Leu
            275                 280                 285

Ser Met Val Glu Lys Arg Met Leu Met Lys Phe Leu Thr Phe Cys Leu
            290                 295                 300

Asp Tyr Glu Gln His Ser Asp Glu Tyr Gln Asp Phe Lys Gln Cys Ser
305                 310                 315                 320

Phe Ser Asp Tyr Leu Lys Thr Lys Lys Leu Thr Pro Asn Leu Gln His
                325                 330                 335

Phe Ile Leu His Ser Ile Ala Met Thr Ser Glu Ser Ser Cys Thr Thr
            340                 345                 350

Leu Asp Gly Leu Gln Ala Thr Lys Thr Phe Leu Gln Cys Leu Gly Arg
            355                 360                 365

Phe Gly Asn Thr Pro Phe Ile Phe Pro Leu Tyr Gly His Gly Glu Ile
            370                 375                 380

Pro Gln Cys Phe Cys Arg Met Cys Ala Val Phe Gly Gly Val Tyr Cys
385                 390                 395                 400

Leu Arg His Lys Val Gln Cys Leu Val Val Asp Lys Asp Ser Gly Arg
                405                 410                 415

Cys Lys Gly Ile Ile Asp Ala Phe Gly Gln Arg Ile Ser Ala Asn Tyr
            420                 425                 430

Phe Ile Val Glu Asp Ser Tyr Leu Pro Lys Glu Thr Cys Ser Asn Val
            435                 440                 445

Gln Tyr Lys Gln Ile Ser Arg Ala Val Leu Ile Thr Asp Gln Ser Ile
            450                 455                 460

Leu Lys Thr Asp Ser Asp Gln Gln Ile Ser Ile Leu Val Val Pro Pro
465                 470                 475                 480

Leu Glu Pro Gly Thr Thr Ser Val Arg Val Met Glu Leu Cys Ser Ser
                485                 490                 495

Thr Met Thr Cys Met Lys Asp Ser Tyr Leu Val His Leu Thr Cys Ser
            500                 505                 510

Ser Ser Lys Thr Ala Arg Glu Asp Leu Glu Pro Val Val Lys Gln Leu
            515                 520                 525

Phe Ile Pro Glu Ala Glu Ala Glu Ala Gly Lys Asp Glu Leu Arg Lys
            530                 535                 540

Pro Arg Leu Leu Trp Ala Leu Tyr Phe Asn Met Arg Asp Ser Ser Gly
545                 550                 555                 560

Val Ser Arg Ser Ser Tyr Cys Gly Leu Pro Ser Asn Val Tyr Ile Cys
                565                 570                 575

Ser Gly Pro Asp Trp Gly Leu Gly Ser Glu His Ala Val Lys Gln Ala
            580                 585                 590

Glu Thr Leu Phe Gln Glu Ile Phe Pro Ser Glu Glu Phe Cys Pro Pro
            595                 600                 605

```
Pro Pro Asn Pro Glu Asp Ile Ile Phe Glu Ala Glu Gly
    610                 615                 620
```

<210> SEQ ID NO 18
<211> LENGTH: 207
<212> TYPE: PRT
<213> ORGANISM: Mus musculus

<400> SEQUENCE: 18

```
Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
    50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
        115                 120                 125

Leu Glu Asn Arg Gln Val Ala Thr Lys Arg Ala Gln Ala Trp Cys Tyr
    130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
            180                 185                 190

Asp Lys Asn Asp Arg Ala Lys Ala Ser Ala Glu Ser Cys Ser Cys
        195                 200                 205
```

<210> SEQ ID NO 19
<211> LENGTH: 1057
<212> TYPE: PRT
<213> ORGANISM: Mus musculus

<400> SEQUENCE: 19

```
Met Leu Cys Trp Gly Asn Ala Ser Tyr Gly Gln Leu Gly Leu Gly Gly
1               5                   10                  15

Ile Asp Glu Glu Ile Val Leu Glu Pro Arg Arg Ser Asp Phe Phe Val
            20                  25                  30

Asn Lys Lys Val Arg Asp Val Gly Cys Gly Leu Arg His Thr Val Phe
        35                  40                  45

Val Leu Asp Asp Gly Thr Val Tyr Thr Cys Gly Cys Asn Asp Leu Gly
    50                  55                  60

Gln Leu Gly His Glu Lys Ser Arg Lys Lys Pro Glu Gln Val Val Ala
65                  70                  75                  80

Leu Asp Ala Gln Asn Ile Val Ala Val Ala Cys Gly Glu Ala His Thr
                85                  90                  95

Leu Ala Leu Asn Asp Lys Gly Gln Val Tyr Ala Trp Gly Leu Asp Ser
            100                 105                 110
```

-continued

```
Asp Gly Gln Leu Gly Leu Gln Gly Ser Glu Glu Cys Ile Arg Val Pro
            115                 120                 125
Arg Asn Ile Lys Ser Leu Ser Asp Ile Gln Ile Val Gln Val Ala Cys
        130                 135                 140
Gly Tyr Tyr His Ser Leu Ala Leu Ser Lys Ala Ser Glu Val Phe Cys
145                 150                 155                 160
Trp Gly Gln Asn Lys Tyr Gly Gln Leu Gly Leu Gly Ile Asp Cys Gln
                165                 170                 175
Lys Gln Thr Ser Pro Gln Leu Ile Lys Ser Leu Leu Gly Ile Pro Phe
            180                 185                 190
Met Gln Val Ala Ala Gly Gly Ala His Ser Phe Val Leu Thr Leu Ser
        195                 200                 205
Gly Ala Ile Phe Gly Trp Gly Arg Asn Lys Phe Gly Gln Leu Gly Leu
210                 215                 220
Asn Asp Glu Asn Asp Arg Tyr Val Pro Asn Leu Leu Lys Ser Leu Arg
225                 230                 235                 240
Ser Gln Lys Ile Val Tyr Ile Cys Cys Gly Glu Asp His Thr Ala Ala
                245                 250                 255
Leu Thr Lys Glu Gly Gly Val Phe Thr Phe Gly Ala Gly Gly Tyr Gly
            260                 265                 270
Gln Leu Gly His Asn Ser Thr Ser His Glu Ile Asn Pro Arg Lys Val
        275                 280                 285
Phe Glu Leu Met Gly Ser Ile Val Thr Gln Val Ala Cys Gly Arg Gln
290                 295                 300
His Thr Ser Ala Phe Val Pro Ser Ser Gly Arg Ile Tyr Ser Phe Gly
305                 310                 315                 320
Leu Gly Gly Asn Gly Gln Leu Gly Thr Gly Ser Thr Ser Asn Arg Lys
                325                 330                 335
Ser Pro Phe Thr Val Lys Gly Asn Trp Phe Ser Tyr Asn Gly Gln Cys
            340                 345                 350
Pro Gln Asp Ile Gly Ser Glu Asp Tyr Phe Cys Val Lys Arg Ile Phe
        355                 360                 365
Ser Gly Gly Asp Gln Ser Phe Ser His Tyr Ser Ser Pro Gln Asn Cys
370                 375                 380
Gly Pro Pro Asp Asp Phe Arg Cys Ser Asp Pro Ser Lys Gln Ile Trp
385                 390                 395                 400
Thr Val Asn Glu Ala Leu Ile Gln Lys Trp Leu Ser Tyr Pro Ser Gly
                405                 410                 415
Arg Phe Pro Val Glu Ile Ala Asn Glu Ile Asp Gly Thr Phe Ser Ser
            420                 425                 430
Ser Gly Cys Leu Asn Gly Ser Phe Leu Ala Ile Ser Asn Asp Asp His
        435                 440                 445
Tyr Arg Thr Gly Thr Arg Phe Ser Gly Val Asp Met Asn Ala Ala Arg
450                 455                 460
Leu Leu Phe His Lys Leu Ile Gln Pro Asp His Pro Gln Ile Ser Gln
465                 470                 475                 480
Gln Val Ala Ala Ser Leu Glu Lys Asn Leu Ile Pro Lys Leu Thr Ser
                485                 490                 495
Ser Leu Pro Asp Val Glu Ala Leu Arg Phe Tyr Leu Thr Leu Pro Glu
            500                 505                 510
Cys Pro Leu Met Ser Asp Cys Asn Asn Phe Thr Thr Ile Ala Ile Pro
        515                 520                 525
Phe Gly Thr Ala Leu Val Asn Leu Glu Lys Ala Pro Leu Lys Val Leu
```

```
                530             535             540
Glu Asn Trp Trp Ser Val Leu Glu Pro Pro Leu Phe Leu Lys Ile Val
545             550             555             560

Glu Leu Phe Lys Glu Val Val His Leu Leu Lys Leu Tyr Lys Ile
                565             570             575

Gly Ile Pro Pro Ser Glu Arg Arg Ile Phe Asn Ser Phe Leu His Thr
                580             585             590

Ala Leu Lys Val Leu Glu Ile Leu His Arg Val Asn Glu Lys Thr Gly
                595             600             605

Gln Leu Ile Gln Tyr Asp Lys Phe Tyr Ile His Glu Val Gln Glu Leu
                610             615             620

Ile Asp Ile Arg Asn Asp Tyr Ile Asn Trp Val Gln Gln Gln Ala Tyr
625             630             635             640

Gly Val Asp Val Ser His Gly Val Thr Glu Leu Ala Asp Ile Pro Val
                645             650             655

Thr Ile Cys Thr Tyr Pro Phe Val Phe Asp Ala Gln Ala Lys Thr Thr
                660             665             670

Leu Leu Gln Thr Asp Ala Val Leu Gln Met Gln Met Ala Ile Asp Gln
                675             680             685

Ala His Arg Gln Asn Val Ser Ser Leu Phe Leu Pro Val Ile Glu Ser
690             695             700

Val Asn Pro Cys Leu Ile Leu Val Val Arg Arg Glu Asn Ile Val Gly
705             710             715             720

Asp Ala Met Glu Val Leu Arg Lys Thr Lys Asn Ile Asp Tyr Lys Lys
                725             730             735

Pro Leu Lys Val Ile Phe Val Gly Glu Asp Ala Val Asp Ala Gly Gly
                740             745             750

Val Arg Lys Glu Phe Phe Leu Leu Ile Met Arg Glu Leu Leu Asp Pro
                755             760             765

Lys Tyr Gly Met Phe Arg Tyr Tyr Glu Asp Ser Arg Leu Ile Trp Phe
                770             775             780

Ser Asp Lys Thr Phe Glu Asp Ser Asp Leu Phe His Leu Ile Gly Val
785             790             795             800

Ile Cys Gly Leu Ala Ile Tyr Asn Phe Thr Ile Val Asp Leu His Phe
                805             810             815

Pro Leu Ala Leu Tyr Lys Lys Leu Leu Lys Arg Lys Pro Ser Leu Asp
                820             825             830

Asp Leu Lys Glu Leu Met Pro Ala Val Gly Arg Ser Met Gln Gln Leu
                835             840             845

Leu Asp Tyr Pro Glu Asp Asp Ile Glu Glu Thr Phe Cys Leu Asn Phe
850             855             860

Thr Ile Thr Val Glu Asn Phe Gly Ala Thr Glu Val Lys Glu Leu Val
865             870             875             880

Leu Asn Gly Ala Asp Thr Ala Val Asn Arg Gln Asn Arg Gln Glu Phe
                885             890             895

Val Asp Ala Tyr Val Asp Tyr Ile Phe Asn Lys Ser Val Ala Ser Leu
                900             905             910

Phe Asp Ala Phe His Ala Gly Phe His Lys Val Cys Gly Gly Lys Val
                915             920             925

Leu Leu Leu Phe Gln Pro Asn Glu Leu Gln Ala Met Val Ile Gly Asn
                930             935             940

Thr Asn Tyr Asp Trp Lys Glu Leu Glu Lys Asn Thr Glu Tyr Lys Gly
945             950             955             960
```

-continued

```
Glu Tyr Trp Ala Asp His Pro Thr Ile Lys Ile Phe Trp Glu Val Phe
            965                 970                 975

His Glu Leu Pro Leu Glu Lys Lys Lys Gln Phe Leu Leu Phe Leu Thr
        980                 985                 990

Gly Ser Asp Arg Ile Pro Ile Leu  Gly Met Lys Ser Leu  Lys Leu Val
        995                 1000                1005

Ile Gln  Ser Thr Gly Gly Gly  Glu Ser Tyr Leu Pro  Val Ser His
    1010                 1015                1020

Thr Cys  Phe Asn Leu Leu Asp  Leu Pro Lys Tyr  Thr  Glu Lys Glu
    1025                 1030                1035

Thr Leu  Arg Cys Lys Leu Ile  Gln Ala Ile Asp  His  Asn Glu Gly
    1040                 1045                1050

Phe Ser  Leu Ile
    1055
```

TRANSGENIC ANIMALS WITH CUSTOMIZABLE TRAITS

CROSS-REFERENCE TO RELATED APPLICATION

This application is a continuation application of Ser. No. 13/768,760, filed Feb. 15, 2013; which claims the priority benefit of U.S. Provisional Application Ser. No. 61/598,987, filed Feb. 15, 2012, which is incorporated herein by reference in its entirety.

The Sequence Listing for this application is labeled SeqList-15Feb13_ST25.txt which was created on Feb. 15, 2013 and is 66 KB. The entire content of the sequence listing is incorporated herein by reference in its entirety.

FIELD OF THE INVENTION

This invention relates to genetic modification of animals in order to effect controlled changes in specified traits such as, for example, changes in skin and/or fur pigmentation.

BACKGROUND OF THE INVENTION

The only pigment synthesized in most animal species, and the only pigment at all in mammalian species, is melanin. There are two classes of melanin: pheomelanin, which produces a blond or red color, and eumelanin, which produces a dark brown or black color. Both classes of melanin are synthesized from tyrosine, but their synthetic pathways diverge after production of dopaquinone.

The primary switch controlling whether a particular melanocyte produces pheomelanin or eumelanin is the melanocortin receptor (MC1R). MC1R polymorphisms also appear to be the primary determinant of red or blond pheomelanin.

The melanocortin receptor can be activated by any of the melanocyte-stimulating hormones (MSH), most commonly by α-MSH, but also by β-defensin 103. Conversely, activation of MC1R can be inhibited through expression of the agouti signaling protein (ASP). The β-defensin 103 signal is dominant over the ASP signal and the ASP signal is dominant over the MSH signal. Further, there are mutations and polymorphisms in all of these genes that increase or decrease their activity. Coat color is further modulated by multiple modulators of melanin production and transport, including tyrosinase (TYR), the tyrosinase transporter OCA2, and the ubiquitination gene HERC2, among others.

Plants make multiple additional classes of pigments, including chlorophyll, carotenoids, anthrocyanins, and betalains. Of these pigments, carotenoids can be most easily transferred to animals because production of carotenoid dyes in plants relies on a precursor that can also be found in animals. Geranylgeranyl pyrophosphate is an intermediate in the HMG-CoA reductase pathway, and is used as a precursor for synthesizing steroids and sterols. With the addition of 4-5 plant proteins, geranylgeranyl pyrophosphate can instead be used as a precursor for synthesizing carotene yellow and orange, or torulene red. The transfer of plant pigments to animals has occurred in nature: the aphid *A. pisum* has several genes somehow transferred from fungi. Carotenoids have also been produced in genetically-engineered yeast, which belong to the animal kingdom.

The only modification of surface pigment ever attempted by genetic intervention in multicellular animals is the wholesale change of animals from light to dark or dark to light. No more detailed patterns have been created. Carotene dyes have never been naturally found in animals more complicated than aphids, and have never been engineered into any multicellular animal. Before the present invention, customizable color or patterns in the skin or fur of animal species have not been created.

BRIEF SUMMARY

The subject invention provides materials and methods for creating customizable traits in animals. For example, the subject invention provides materials and methods for creating customizable patterns in the skin and/or fur of animals. In other embodiments, the customizable trait can involve the length and/or texture of animal skin or fur. Alternatively, the subject invention can be used to effect controlled changes in the texture, structural strength, and/or length of animal nail, claw, and/or horn.

In one specific embodiment, the methods of the subject invention comprise introducing into the cells of an animal a genetic construct comprising a keratin-14 specific promoter, red fluorescent protein in a loxp cassette, dominant black (ΔG23) beta defensin 103 in a pigment cassette, and an SV40 (with intron) polyadenylation sequence. When a composition comprising Cre recombinase (or HTNCre) is then applied to the skin of an animal having the genetic construct, the fur of the animal will turn black where the composition was applied. In this way, the fur is permanently genetically modified to turn color in a desired shape.

Thus, in one embodiment the subject invention provides a method of creating customizable permanent patterns in the skin and/or fur of animals.

In another embodiment the subject invention provides methods for producing multicolor patterns in the skin and/or fur of animal species.

In a further embodiment the subject invention provides a method of creating customizable patterns in the skin and/or fur of animal species such that the animal would continue to grow fur to sustain those colors throughout its lifetime.

The invention also provides methods of creating customizable predefined patterns of stripes that are heritable within that animal.

In one embodiment, the present invention provides transdermal application of one or more activating factors to drive recombination and permanent transgene expression in the transgenic animals of the present invention. In certain specific embodiments, the activating factors useful according to the present invention include, but are not limited to, recombinase proteins, small molecules (such as, doxycycline, cumate, ecdysone, etc) capable of inducing the expression of recombinase, viruses that capable of inducing the expression of recombinase, and nucleic acid (such as DNA) constructs that drive the expression of recombinase.

In certain embodiments, the activating factor is applied to the surface of the animal skin, either alone or in a carrier solution (e.g., liposomes, solvents, mixtures containing DMSO, etc.). In one embodiment, the activating factor is applied intradermally (such as with the use of a tattoo needle) or subdermally.

In one embodiment, the transgenic animal comprises one or more exogenous nucleic acid molecules including, but not limited to, pigmentation-related genes, coat/hair quality genes (such as genes for controlling the length and/or curliness of animal hair), genes related to nail/claw or horn quality (such as a nucleic acid molecule encoding crosslinking keratin), and genes for synthesis and/or expression of plant pigments in animal cells.

In certain embodiments, promoters useful according to the present invention include, but are not limited to, skin-specific promoters (e.g., keratin specific promoter), melanocyte specific promoters (e.g., MCR promoter), constitutive promoters (e.g., beta-globin promoter, CMV promoter), and promoters responsive to circulating factors such as NF-kB, interferon gamma, estrogen, and glucocorticoids.

In certain embodiments, the present invention provides the use of multiple types of recombinase targets to allow specific activation of different genes selectively through application of different recombinases. In one embodiment, multiple recombinase targets are used to allow multiple colors to be created after birth of the animal.

In one embodiment, in a transgenic dog with a naturally golden fur, Cre recombinase activates the production of dog fur with black color, and Flp recombinase activates the production of dog fur with red color.

In one embodiment, the present invention provides the use of native promoters to drive coat pigmentation without the need for an external activating factor. In a specific embodiment, the native promoter relates to defining somite boundaries in animal development.

In one embodiment, the native heterologous promoter is used to create coat patterns in a different species, such as, for example, using the Tabby or Ticked promoters found in cats to drive coat coloration in dogs.

In certain embodiments, the present invention provides genetically modified animals with coat patterns that are permanently customizable after birth.

In certain embodiments, the present invention provides genetically modified animals with coat colors not normally found in mammals.

In certain embodiments, the present invention provides genetically modified cattle, sheep or other animals that have permanent identification marks (such as, a number or a bar code) growing in their coat.

In certain embodiments, the present invention provides genetically modified cattle, sheep or other animals that have "invisible" marks in their coat that can change color in response to changes in health or physiological conditions.

In one embodiment, the transgenic cattle or sheep or other animals can express one symbol on the coat or fur, wherein that symbol can change color if the animal has chronic activation of NF-kB, and another symbol that can change color if the animal has chronic activation of interferon-gamma.

In certain embodiments, the present invention provides genetically modified animals born with coat colors and patterns not normally found in their native species.

BRIEF DESCRIPTION OF THE SEQUENCES

Figure 1:
FIG. 1 is a schematic depiction of an embodiment of a genetic construct for effecting color change in animals.

SEQ ID NO:1 is the amino acid sequence of a bifunctional enzyme CarRP-like isoform 1 [*Acyrthosiphon pisum*] (GenBank Accession No. XP_001943170).

SEQ ID NO:2 is the amino acid sequence of a bifunctional enzyme CarRP-like [*Acyrthosiphon pisum*] (GenBank Accession No. XP_001950787).

SEQ ID NO:3 is the amino acid sequence of a lycopene cyclase/phytoene synthase-like [*Acyrthosiphon pisum*] (GenBank Accession No. XP_001950868).

SEQ ID NO:4 is the amino acid sequence of a phytoene dehydrogenase-like [*Acyrthosiphon pisum*] (GenBank Accession No. XP_001943225).

SEQ ID NO:5 is the amino acid sequence of a phytoene dehydrogenase-like [*Acyrthosiphon pisum*] (GenBank Accession No. XP_001950764).

SEQ ID NO:6 is the amino acid sequence of a phytoene dehydrogenase-like [*Acyrthosiphon pisum*] (Genbank Accession No. XP001946689).

SEQ ID NO:7 is the amino acid sequence of a phytoene dehydrogenase-like [*Acyrthosiphon pisum*] (Genbank Accession No. XP_001943938).

SEQ ID NO:8 is the amino acid sequence of a melanocortin 1 receptor (GenBank Accession No. EDL11741).

SEQ ID NO:9 is the amino acid sequence of an alpha melanocyte stimulating hormone (MSH).

SEQ ID NO:10 is the amino acid sequence of a beta melanocyte stimulating hormone (MSH).

SEQ ID NO:11 is the amino acid sequence of a beta melanocyte stimulating hormone (MSH).

SEQ ID NO:12 is the amino acid sequence of a gamma melanocyte stimulating hormone (MSH).

SEQ ID NO:13 is the amino acid sequence of a β-defensin protein (GenBank Accession No. AAT67592).

SEQ ID NO:14 is the amino acid sequence of an agouti signaling protein precursor (GenBank Accession No. NP_056585).

SEQ ID NO:15 is the amino acid sequence of a tyrosinase (TYR) (GenBank Accession No. BAA00341).

SEQ ID NO:16 is the amino acid sequence of a melanocyte-specific transporter protein (GenBank Accession No. Q62052).

SEQ ID NO:17 is the amino acid sequence of a rab protein geranylgeranyltransferase component A2 (GenBank Accession No. NP_067325).

SEQ ID NO:18 is the amino acid sequence of a ras-related protein Rab-7a (GenBank Accession No. NP_033031).

SEQ ID NO:19 is the amino acid sequence of a probable E3 ubiquitin-protein ligase (HERC2) (GenBank Accession No. NP_084390).

DETAILED DISCLOSURE

The subject invention provides materials and methods for creating customizable traits in animals. For example, the subject invention provides materials and methods for creating customizable patterns in the skin and/or fur of animals. In other embodiments, the customizable trait can involve the length and/or texture of animal skin or fur. Alternatively, the subject invention can be used to effect controlled changes in the texture, structural strength, and/or length of animal hair, nail, claw and/or horn.

In one specific embodiment, the methods of the subject invention comprise introducing into the cells of an animal a genetic construct comprising a keratin-14 specific promoter, red fluorescent protein in a loxp cassette, dominant black (ΔG23) beta defensin 103 in a pigment cassette, and an SV40 (with intron) polyadenylation sequence. When a composition comprising Cre recombinase (or HTNCre) is then applied to the skin of an animal having the genetic construct, the fur of the animal turns black where the composition is applied. In this way, the fur is permanently genetically modified to turn color in a desired shape.

Thus, in one embodiment the subject invention provides a method of creating customizable permanent patterns in the skin and/or fur of animals.

In another embodiment the subject invention provides methods for producing multicolor patterns in the skin and/or fur of animal species.

In a further embodiment the subject invention provides a method of creating customizable patterns in the skin and/or fur of animal species such that the animal would continue to grow fur to sustain those colors throughout its lifetime.

The invention also provides methods of creating customizable predefined patterns of stripes that are heritable within that animal.

In one embodiment, the transgenic animal has heritable soft claws or soft hair or fur.

In another embodiment, the present invention provides cells, tissues, or parts (such as skin, hair, fur) of the transgenic animal, and uses thereof. In one embodiment, the transgenic animal has customizable color and/or patterns in the skin and/or fur, and the skin or fur can be subsequently removed from the transgenic animal for production of hides, fur, leather, etc, useful for production of clothing, rugs, shoes, horse tack, horse harness, upholstery, and other leather goods.

Transgenic Animals with Customizable Traits

In one embodiment, the present invention provides a transgenic animal with customizable traits, wherein the transgenic animal (such as in its genome) comprises:

an exogenous nucleic acid molecule encoding a protein of interest, wherein the nucleic acid molecule is operably linked to a promoter and is under the control of an inducible gene expression system that requires the presence of an inducing agent to activate gene expression;

wherein the expression of the exogenous nucleic acid molecule is inhibited in the absence of the inducing agent.

In certain embodiments, the exogenous nucleic acid molecule that encodes a protein is selected from pigment proteins; proteins involved in the synthesis and/or transport of pigments; luminescent (such as fluorescent) proteins; proteins involving the length and/or texture of animal skin or fur; and proteins involved in the texture, structural strength, and/or length of animal nail, claw, and/or horn.

In one specific embodiment, the present invention provides a transgenic animal with customizable fur or skin pigmentation, wherein the genome of the transgenic animal comprises:

an exogenous nucleic acid molecule encoding a pigment protein of interest or a protein involved in the synthesis and/or transport of a pigment of interest, wherein the exogenous nucleic acid molecule is operably linked to a promoter and is under the control of an inducible gene expression system that is a site-specific recombination system, wherein the site-specific recombination system inhibits the expression of the first nucleic acid molecule in the absence of site-specific recombination.

The expression of the exogenous nucleic acid molecule can be induced after the application of, for example, a recombinase to the transgenic animal.

In one embodiment, the exogenous nucleic acid molecule, the promoter, and/or the site-specific recombination system are contained in a pigmentation construct.

In one embodiment, the genome of the transgenic animal comprises an exogenous nucleic acid molecule whose expression is under the control of a Cre/LoxP recombination system, wherein the Cre/LoxP recombination system prevents the expression of the exogenous nucleic acid molecule. In one specific embodiment, the Cre/LoxP recombination system comprises a lox-stop-lox (LSL) sequence.

In one embodiment, the pigmentation construct is transferred into cells, such as fertilized ova. The pigmentation construct can be transferred into fertilized ova using any conventional means, including, but not limited to, lentivirii, pronuclear injections, and intracytoplasmic sperm injection (ICSI).

In certain embodiments, one or more pigmentation constructs are introduced into the genome of the transgenic animal. The pigmentation construct can comprise more than one exogenous nucleic acid molecule, each nucleic acid molecule encoding a protein of interest.

In certain embodiments, the genome of the transgenic animal comprises more than one inducible gene expression systems to control the expression of the nucleic acid molecules of interest.

In one specific embodiment, the present invention provides a transgenic animal with customizable traits (such as fur or skin pigmentation), wherein the genome of the transgenic animal comprises:

a first exogenous nucleic acid molecule encoding a protein of interest (such as a pigmentation protein) operably linked to a first promoter and under the control of a loxP site, wherein the loxP site prevents the expression of the first exogenous nucleic acid molecule in the absence of Cre recombinase protein; and a second nucleic acid molecule encoding a Cre recombinase protein, operably linked to a second promoter.

In another specific embodiment, the present invention provides a transgenic animal with customizable traits (such as fur or skin pigmentation), wherein the genome of the transgenic animal comprises:
- a first exogenous nucleic acid molecule encoding a protein of interest (such as pigmentation protein) operably linked to a first promoter and under the control of a loxP site, wherein the loxP site prevents the expression of the first nucleic acid molecule in the absence of Cre recombinase protein;
- a second nucleic acid encoding a reverse tRA (rtTA), operably linked to a second promoter; and
- a third nucleic acid molecule encoding a Cre recombinase protein, operably linked to a third promoter under the control of a TetO operator.

Figure 2:
FIG. 2 is a schematic depiction of an embodiment of a genetic construct for creating customizable patterns and color in animal skin or fur.
Figure 3:
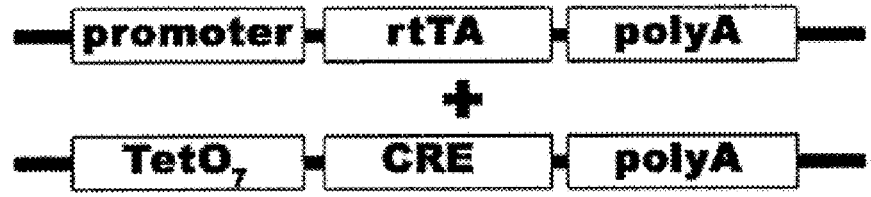
FIG. 3 is a schematic depiction of an embodiment of genetic constructs for creating customizable patterns and color in animal skin or fur.

FIGS. 2 and 3 show an embodiment of the expression constructs, wherein the expression of the exogenous nucleic acid molecule of interest (such as pigment proteins and proteins involved in the synthesis of biological pigments) is under the control of the Cre-LoxP recombination system and a tetracycline (Tet)-controlled transcription activation system.

In one specific embodiment, doxycycline (or ecdysone, etc) mixed with DMSO carrier is applied to a transgenic animal with a gold fur color, whereby the color of the transgenic animal turns red; subsequently, Cre or HTNCre mixed with DMSO is applied to the transgenic animal to produce a black color.

In another specific embodiment, the genome of the transgenic animal comprises an exogenous nucleic acid molecule the expression of which is under the control of a tetracycline (Tet)-controlled transcriptional activation system.

In another embodiment, the present invention provides a transgenic animal with customizable traits (such as fur or skin pigmentation), wherein the genome of the transgenic animal comprises: a first exogenous nucleic acid molecule encoding a protein of interest (such as a pigmentation protein) operably linked to a first promoter and under the control of an inducible gene expression system (e.g., a tetracycline (Tet)-controlled transcriptional activation system), wherein the inducible gene expression system, in its inactivated state (absent of induction), prevents the expression of the first nucleic acid molecule.

The transgenic animal can be of any species, including, but not limited to, mammalian species including, but not limited to, domesticated and laboratory animals such as dogs, cats, mice, rats, guinea pigs, and hamsters; livestock such as horses, cattle, pigs, sheep, goats, ducks, geese, and chickens; primates such as apes, chimpanzees, orangutans, humans, and monkeys; fish; amphibians such as frogs and salamanders; reptiles such as snakes and lizards; and other animals such as fox, weasels, rabbits, mink, beavers, ermines, otters, sable, seals, coyotes, chinchillas, deer, muskrats, and possum. In certain embodiments, the animal is not a human.

Pigment Proteins

The term "pigment protein," as used herein, refers to a protein comprising a pigment. The term "pigment," as used herein, refers to a material that does not emit light but changes the color of reflected or transmitted light as the result of wavelength-selective absorption; this physical process differs from fluorescence, phosphorescence, and other forms of luminescence, in which a material emits light. Pigment proteins include, but are not limited to, chromoproteins such as cytochromes and flavoproteins.

Luminescent Proteins

The term "luminescent protein," as used herein, refers to a protein that emits light. Luminescent proteins useful according to the present invention include, but are not limited to, fluorescent proteins including, but not limited to, green fluorescent protein, yellow fluorescent protein, cyan fluorescent protein, and red fluorescent protein; and phosphorescent proteins. Fluorescent proteins are members of a class of proteins that share the unique property of being self-sufficient to form a visible wavelength chromophore from a sequence of three amino acids within their own polypeptide sequence. A variety of luminescent proteins, including fluorescent proteins, are publicly known. Fluorescent proteins useful according to the present invention include, but are not limited to, the fluorescent proteins disclosed in U.S. Pat. No. 7,160,698, U.S. Application Publication Nos. 2009/0221799, 2009/0092960, 2007/0204355, 2007/0122851, 2006/0183133, 2005/0048609, 2012/0238726, 2012/0034643, 2011/0269945, 2011/0223636, 2011/0152502, 2011/0126305, 2011/0099646, 2010/0286370, 2010/0233726, 2010/0184116, 2010/0087006, 2010/0035287, 2007/0021598, 2005/0244921, 2005/0221338, 2004/0146972, and 2001/0003650, all of which are hereby incorporated by reference in their entireties.

Proteins Involved in the Synthesis of Biological Pigments

Proteins involved in the synthesis of biological pigments include, but are not limited to, the wild-type or mutant forms of melanocortin receptor (MC1R), melanocyte stimulating hormones (MSH) (e.g., α-MSH, β-MSH, γ-MSH), β-defensin 103, agouti signaling protein (ASP), tyrosinase (TYR), melanocyte-specific transporter protein, Ras-related protein Rab-7, rab protein geranylgeranyltransferase component A2, and probable E3 ubiquitin-protein ligase (HERC2).

In certain embodiments, the genome of the transgenic animal comprises an exogenous nucleic acid molecule encoding a protein involved in the synthesis of a biological pigment.

Nucleic acid molecules encoding proteins involved in the synthesis and/or transport of biological pigments can be derived from genes including, but not limited to, the dominant MC1R E92K and the agouti gene. In certain embodiments, the genome of the transgenic animal comprises a nucleic acid molecule encoding a protein involved in the synthesis and/or transport of biological pigments including, but not limited to, melanins (e.g., pheomelanin, eumelanin); urochrome; chlorophyll; bilirubin; biliverdin; phycobilin; phycoerythrobilin; stercobilin; urobilin; hemocyanin; hemoglobin; myoglobin; luciferins; carotenoids, including hematochromes, carotenes (e.g., alpha and beta carotene, lycopene, rhodopsin), xanthophylls (e.g., canthaxanthin, zeaxanthin, lutein); phytochrome; phycobiliproteins (e.g., R-phycoerythrin (R-PE), B-phycoerythrin (B-PE), C-phycocyanin (CPC), allophycocyanin (APC)); polyene enolates; and flavonoids.

Carotenoid pigments in yellow, red, or orange can be synthesized in animals that express phytoenesynthases, desaturases, and cyclases, as described in Moran (2010) and Verdoes (2003). In one embodiment, the carotenoid dyes are synthesized using geranylgeranyl pyrophosphate as a substrate.

Proteins involved in the synthesis and/or transport of biological pigments include, but are not limited to, bifunctional enzyme CarRP-like isoform 1 [*Acyrthosiphon pisum*] (such as, GenBank Accession No. XP_001943170 (SEQ ID NO:1)), bifunctional enzyme CarRP-like [*Acyrthosiphon pisum*] (such as, GenBank Accession No. XP_001950787

(SEQ ID NO:2)), lycopene cyclase/phytoene synthase-like [*Acyrthosiphon pisum*] (such as GenBank Accession No. XP_001950868 (SEQ ID NO:3)), phytoene dehydrogenase-like [*Acyrthosiphon pisum*] (such as, GenBank Accession No. XP_001943225 (SEQ ID NO:4)), phytoene dehydrogenase-like [*Acyrthosiphon pisum*] (such as, GenBank Accession No. XP_001950764 (SEQ ID NO:5)), phytoene dehydrogenase-like [*Acyrthosiphon pisum*] (such as, GenBank Accession No. XP001946689 (SEQ ID NO:6)), and phytoene dehydrogenase-like [*Acyrthosiphon pisum*] (such as, GenBank Accession No. XP_001943938 (SEQ ID NO:7)).

Proteins involved in the synthesis and/or transport of biological pigments can be of any animal origin (such as mouse, porcine, human) including, but not limited to, melanocortin 1 receptor (such as, GenBank Accession No. EDL11741 (SEQ ID NO:8)), alpha melanocyte stimulating hormones (MSH) (such as, SEQ ID NO:9), beta melanocyte stimulating hormones (MSH) (such as, SEQ ID NO:10, SEQ ID NO:11), gamma melanocyte stimulating hormones (MSH) (such as, SEQ ID NO:12), β-defensin (such as, GenBank Accession No. AAT67592 (SEQ ID NO:13)), agouti signaling protein precursor (such as, GenBank Accession No. NP_056585 (SEQ ID NO:14)), tyrosinase (TYR) (such as, GenBank Accession No. BAA00341 (SEQ ID NO:15)), melanocyte-specific transporter protein (such as, GenBank Accession No. Q62052 (SEQ ID NO:16)), rab proteins geranylgeranyltransferase component A2 (such as, GenBank Accession No. NP_067325 (SEQ ID NO:17)), ras-related protein Rab-7a (such as, GenBank Accession No. NP_033031 (SEQ ID NO:18)), and probable E3 ubiquitin-protein ligase (HERC2) (such as, GenBank Accession No. NP_084390 (SEQ ID NO:19)).

In certain embodiments, proteins involved in the synthesis and/or transport of biological pigments can be proteins having at least 80% identity, or having any percent identity higher than 80% (such as at least 85%, 87%, 90%, 92%, 93%, 94%, 95%, 96%, 97%, 98%, or 99%), to any of SEQ ID NOs: 1-19.

Proteins Involved in the Texture, Structural Strength, and/or Length of Hair, Nail, Claw and/or Horn In certain embodiment, the transgenic animal expresses a nucleic acid molecule encoding a protein that alters hair quality (such as straight or curly hair) or length. In one embodiment, conditional over-expression of WNT3 or DVL2 in the outer root sheath induces shorter hair in animals. In certain embodiments, the transgenic animal expresses a nucleic acid molecule encoding a protein involves that the texture, structural strength, and/or length of animal hair, nail, claw and/or horn.

Proteins involved in controlling the texture, structural strength, and/or length of animal hair, nail, claw and/or horn include keratin proteins, including, but not limited to, keratin 1, keratin 2, keratin 2A, keratin HB6, keratin 3, keratin 4, keratin 5, keratin 6, keratin 7, keratin 8, keratin 9, keratin 10, keratin 11, keratin 12, keratin 13, keratin 14, keratin 15, keratin 16, keratin 17, keratin 18, keratin 19, keratin 20, keratin 23, keratin 24, keratin 25, keratin 26, keratin 27, keratin 28, keratin 31, keratin 32, keratin 33, keratin 34, keratin 35, keratin 36, keratin 37, keratin 38, keratin 39, keratin 40, keratin 71, keratin 72, keratin 73, keratin 74, keratin 75, keratin 76, keratin 77, keratin 78, keratin 79, keratin 80, keratin 81, keratin 82, keratin 83, keratin 84, keratin 85, and keratin 86.

Modification of Amino Acid and/or Polynucleotide Sequences

The amino acid sequences of a variety of pigment proteins; proteins involved in the synthesis and/or transport of pigments; proteins involving the length and/or texture of animal skin or fur; and proteins involved in the texture, structural strength, and/or length of animal nail, claw, and/or horn, are publicly available, such as via the GenBank database. The present invention encompasses the use of such proteins.

Polynucleotides and polypeptides within the scope of the subject invention can also be defined in terms of identity with those sequences that are specifically exemplified herein. The sequence identity will typically be greater than 60%, preferably greater than 75%, more preferably greater than 80%, even more preferably greater than 90%, and can be greater than 95%. The identity of a sequence can be 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

Promoter Elements

In certain embodiments in accordance with the present invention, the nucleic acid molecule is operably linked to a constitutive, inducible, or tissue-specific promoter.

The term "constitutive promoter," as used herein, refers to its ordinary meaning that is an unregulated promoter that allows for continual transcription of its associated gene. Constitutive promoters useful according to the present invention include, but are not limited to, cytomegalovirus (CMV) promoter, CMV-chicken beta actin promoter, ubiquitin promoter, JeT promoter, SV40 promoter, beta globin promoter, elongation Factor 1 alpha (EF1-alpha) promoter, RSV promoter, and Mo-MLV-LTR promoter.

Promoters useful according to the present invention include, but are not limited to, universal promoters (e.g., *Rosa*26); tissue-specific promoters, such as keratinocyte specific promoters (e.g., Keratin 14); melanocyte specific promoters (e.g., promoter of the melanocortin 1 receptor (MCR1) gene); and dermal papilla-specific promoters. Promoters useful according to the present invention include melanocyte specific promoters and matrix-cell specific promoters.

Keratinocyte specific promoters include, but are not limited to, promoters of keratin 1, keratin 2, keratin 2A, keratin HB6, keratin 3, keratin 4, keratin 5, keratin 6, keratin 7, keratin 8, keratin 9, keratin 10, keratin 11, keratin 12, keratin 13, keratin 14, keratin 15, keratin 16, keratin 17, keratin 18, keratin 19, keratin 20, keratin 23, keratin 24, keratin 25, keratin 26, keratin 27, keratin 28, keratin 31, keratin 32, keratin 33, keratin 34, keratin 35, keratin 36, keratin 37, keratin 38, keratin 39, keratin 40, keratin 71, keratin 72, keratin 73, keratin 74, keratin 75, keratin 76, keratin 77, keratin 78, keratin 79, keratin 80, keratin 81, keratin 82, keratin 83, keratin 84, keratin 85, and keratin 86 gene.

In certain embodiments, promoters useful according to the present invention include, but are not limited to, promoters inducing gene expression in the presence of an endogenous biological factor of interest, such as NF-KB, interferon-gamma, estrogen, and or glucocorticoids.

Promoters useful according to the present invention include, but are not limited to, promoters inducing gene expression in the presence of an infectious agent of interest, such as a virus, bacteria, and/or protozoa.

In one embodiment, a dermal papilla-specific promoter is used for creating customizable pigmentation, color, or pattern in cells derived from somites; useful promoters include, but are not limited to, a Ripply2 promoter, a Tabby promoter, and a Ticked promoter. The choice of promoters can be determined by performing multiple species comparisons and/or using the extent of well-conserved promoter elements. In certain embodiments, the promoter element further comprises a nucleic acid molecule encoding a reporter protein, which is expressed in response to the administration of drugs, and/or a metabolic state or circulating levels of biomarkers in the transgenic animal. In one embodiment, the promoter induces expression of a protein of interest (such as a pigment protein and/or a protein involved in the synthesis of a biological pigment) in response to the presence of a physiological state of interest in the transgenic animal, such as for example, cardiac stress, increased levels of circulating cytokines, and/or increased steroid presence or activity.

Inducible Expression Systems

The inducible gene expression systems useful according the present invention include, but are not limited to, site-specific recombination systems including, but not limited to, a Cre-LoxP recombination system, a FLP-FRT recombination system; a tetracycline (Tet)-controlled transcription activation system; an ecdysone inducible system; a heat shock on/off system; a lacO/IPTG system; a cumate repressor protein CymR system; a nitroreductase system; coumermycin/novobiocin-regulated system; a RheoSwitch Ligand RSL1 system; a chimeric bipartite nuclear receptor expression system; a GAL4 system; sterol or steroid or synthetic steroid inducing/repressing system; and any combination thereof.

In one embodiment, the inducible system useful according to the present invention is a Cre-LoxP recombination system. The genome of the transgenic animal can comprise an exogenous nucleic acid molecule whose expression is under the control of a Cre/LoxP recombination system, wherein the Cre/LoxP recombination system prevents the expression of the exogenous nucleic acid molecule. In one specific embodiment, the Cre/LoxP recombination system comprises a lox-stop-lox (LSL) sequence.

The Cre-LoxP recombination system is a site-specific recombination technology useful for performing site-specific deletions, insertions, translocations, and inversions in the DNA of cells or transgenic animals. The Cre recombinase protein (encoded by the locus originally named as "causes recombination") consists of four subunits and two domains: a larger carboxyl (C-terminal) domain and a smaller amino (N-terminal) domain. The loxP (locus of X-over P1) is a site on the Bacteriophage P1 and consists of 34 bp. The results of Cre-recombinase-mediated recombination depend on the location and orientation of the loxP sites, which can be located cis or trans. In case of cis-localization, the orientation of the loxP sites can be the same or opposite. In case of trans-localization, the DNA strands involved can be linear or circular. The results of Cre recombinase-mediated recombination can be excision (when the loxP sites are in the same orientation) or inversion (when the loxP sites are in the opposite orientation) of an intervening sequence in case of cis loxP sites, or insertion of one DNA into another or translocation between two molecules (chromosomes) in case of trans loxP sites. The Cre-LoxP recombination system is known in the art, see, for example, Andras Nagy, Cre recombinase: the universal reagent for genome tailoring, *Genesis* 26:99-109 (2000).

The Lox-Stop-Lox (LSL) cassette prevents expression of the transgene in the absence of Cre-mediated recombination. In the presence of Cre recombinase, the LoxP sites recombine, and the stop cassette is deleted. The Lox-Stop-Lox (LSL) cassette is known in the art. See, Allen Institute for Brain Science, Mouse Brain Connectivity Altas, Technical White Paper: Transgenic Characterization Overview (2012).

In certain embodiments, the loxP site further comprises a reporter gene encoding gene (e.g., lacz, GFP) and/or a nucleic acid molecule encoding a second pigmentation protein (e.g., if the first pigmentation contains a dominantly active MC1R, another agouti gene could be flanked by the loxP site).

Tetracycline (Tet)-controlled transcriptional activation is a method of inducible expression where transcription is reversibly controlled by the presence or absence of the antibiotic tetracycline or one of its derivatives (e.g., doxycycline). Gene expression is activated as a result of binding of the Tet-off or Tet-on protein to tetracycline response elements (TREs) located within an inducible promoter. Both the Tet-on and Tet-off proteins activate gene expression. The Tet-Off protein activates gene expression in the absence of a tetracycline derivative-doxycycline (Dox), whereas the Tet-on protein activates gene expression in the presence of Dox.

In the Tet-off system, the tetracycline transactivator (tTA) protein, which is created by fusing the TetR (tetracycline repressor) protein (obtainable from *Escherichia coli* bacteria) with the VP16 protein (obtainable from the Herpes Simplex Virus), binds on DNA at a TetO operator. Once bound the TetO operator activates the promoter coupled to the TetO operator, thereby activating the transcription of the nearby gene. Tetracycline derivatives bind tTA and render it incapable of binding to TRE sequences, thereby preventing transactivation of target genes.

In the Tet-On system, when the tTA protein is bound by doxycycline, the doxycycline-bound tTA is capable of binding the TetO operator. Thus, the introduction of doxycyline to the system initiates the transcription of the genetic product. The Tet-on system is sometimes preferred for the faster responsiveness.

The reverse tTA (rtTA) is a complementary genetic module for rapid gene activation by addition of Dox (Tet-on). See Kistner et al., Doxycycline-mediated quantitative and tissue-specific control of gene expression in transgenic mice, *Proc. Natl. Acad. Sci. U.S.A.* Vol. 93, pp. 10933-10938 (1996).

The Tet-on advanced transactivator (also known as rtTA2$^S$-M2) is an alternative version of Tet-On that shows reduced basal expression, and functions at a 10-fold lower Dox concentration than Tet-on. In addition, its expression is considered to be more stable in eukaryotic cells due to being human codon optimized and utilizing three minimal transcriptional activation domains. Tet-on 3G (also known as rtTA-V10) is similar to Tet-on Advanced, and is human codon optimized and composed of three minimal VP16 activation domains. The Tet-on 3G is sensitive to 100-fold less Dox than the original Tet-on.

In one embodiment of a tetracycline-responsive regulatory expression element, a tetracycline-controlled reverse transactivator (rtTA) comprises a tetR (e.g., from *Escherichia coli* Tn10); a mammalian transcription factor VP 16 transactivating domain serving as an effector; and a tissue-specific promoter controlling the rtTA effector transcription. In the presence of doxycycline, the rtTA binds to a (TeTO)$_7$ operator (a seven tandemly repeated TetO sequence) placed upstream of a CMV promoter that drives expression of a transgene. As a result, transgene expression can be switched on or off by administration and withdrawal of doxycycline.

Expression Constructs

The present invention also provides expression constructs, vectors, as well as host cells useful for producing transgenic animals.

As used herein, the term "expression construct" refers to a combination of nucleic acid sequences that provides for transcription of an operably linked nucleic acid sequence. Expression constructs of the invention also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

In certain embodiments, the present invention provides expression constructs for customizing color and/or pattern of animals, including pigmentation constructs and patterning constructs.

FIG. 1 shows an embodiment of a pigmentation construct comprising a promoter, a loxP cassette, a nucleic acid molecule encoding a pigment protein of interest or a protein involved in the synthesis and/or transport of a pigment of interest, and polyadenylation sequence. In one embodiment of the pigmentation construct, the expression of the pigment protein of interest or a protein involved in the synthesis and/or transport of a pigment of interest is activated by application of Cre recombinase.

In another embodiment, the present invention provides a pattern construct. FIG. 2 shows an embodiment of a patterning construct. In one embodiment, the promoter of the patterning construct is derived from a gene specific to somite boundary specification. In one embodiment, the promoter is selected from a Ripply2 promoter, a Tabby promoter, and a Ticked promoter. In one embodiment, the transgenic animal comprises a pigmentation construct and a patterning construct. In one embodiment, the transgenic animal has customizable constitutive vertical stripes on the dorsal dermis.

In one embodiment, the genome of the transgenic animal comprises:
1) pigmentation construct as shown in FIG. 1, wherein the promoter is a melanocyte-specific promoter and the nucleic acid molecule encodes a protein involved in the synthesis of a red pigment (such as ASIP or MC1R);
2) a pigmentation construct as shown in FIG. 1, wherein the promoter is a dermal papilla-specific promoter and the nucleic acid molecule encodes—defensin 103; and
3) a set of constructs as shown in FIG. 3, wherein the promoter is a melanocyte-specific promoter.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

As used herein, the term "operably linked" refers to a juxtaposition of the components described wherein the components are in a relationship that permits them to function in their intended manner. In general, operably linked components are in contiguous relation. Sequence(s) operably-linked to a coding sequence may be capable of effecting the replication, transcription and/or translation of the coding sequence. For example, a coding sequence is operably-linked to a promoter when the promoter is capable of directing transcription of that coding sequence.

A "coding sequence" or "coding region" is a polynucleotide sequence that is transcribed into mRNA and/or translated into a polypeptide. For example, a coding sequence may encode a polypeptide of interest. The boundaries of the coding sequence are determined by a translation start codon at the 5'-terminus and a translation stop codon at the 3'-terminus.

The term "promoter," as used herein, refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

In addition to a promoter, one or more enhancer sequences may be included such as, but not limited to, cytomegalovirus (CMV) early enhancer element and an SV40 enhancer element. Additional included sequences are an intron sequence such as the beta globin intron or a generic intron, a transcription termination sequence, and an mRNA polyadenylation (pA) sequence such as, but not limited to, SV40-pA, beta-globin-pA, the human growth hormone (hGH) pA and SCF-pA.

In one embodiment, the expression construct comprises polyadenylation sequences, such as polyadenylation sequences derived from bovine growth hormone (BGH) and SV40.

The term "polyA" or "p(A)" or "pA" refers to nucleic acid sequences that signal for transcription termination and mRNA polyadenylation. The polyA sequence is characterized by the hexanucleotide motif AAUAAA. Commonly used polyadenylation signals are the SV40 pA, the human growth hormone (hGH) pA, the beta-actin pA, and beta-globin pA. The sequences can range in length from 32 to 450 bp. Multiple pA signals may be used.

In one embodiment, the genetic construct comprises a nucleic acid molecule encoding a selection marker, such as neomycin resistance biomarker protein, which can be excised through PIGGYBAC™ transposons. In one embodiment, the construct is flanked by short homology arms.

The term "vector" is used to refer to any molecule (e.g., nucleic acid, plasmid, or virus) used to transfer coding information (e.g., a polynucleotide of the invention) to a host cell.

The terms "expression vector" and "transcription vector" are used interchangeably to refer to a vector that is suitable for use in a host cell (e.g., a subject's cell) and contains nucleic acid sequences that direct and/or control the expression of exogenous nucleic acid sequences. Expression includes, but is not limited to, processes such as transcription, translation, and RNA splicing, if introns are present. Vectors useful according to the present invention include plasmids, viruses, BACs, YACs, and the like. Particular viral vectors illustratively include those derived from adenovirus, adeno-associated virus and lentivirus.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

The term "recombinant" is used to indicate a nucleic acid construct in which two or more nucleic acids are linked and which are not found linked in nature.

The term "nucleic acid" as used herein refers to RNA or DNA molecules having more than one nucleotide in any form including single-stranded, double-stranded, oligonucleotide or polynucleotide.

The term "nucleotide sequence" is used to refer to the ordering of nucleotides in an oligonucleotide or polynucleotide in a single-stranded form of nucleic acid.

The term "expressed" refers to transcription of a nucleic acid sequence to produce a corresponding mRNA and/or translation of the mRNA to produce the corresponding protein. Expression constructs can be generated recombinantly or synthetically or by DNA synthesis using well-known methodology.

The term "regulatory element" as used herein refers to a nucleotide sequence which controls some aspect of the expression of an operably linked nucleic acid sequence. Exemplary regulatory elements illustratively include an enhancer, an internal ribosome entry site (IRES), an intron, an origin of replication, a polyadenylation signal (pA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation.

In one embodiment, the construct of the present invention comprises an internal ribosome entry site (IRES). In one embodiment, the expression construct comprises kozak consensus sequences.

Optionally, a reporter gene is included in the transgene construct. The term "reporter gene" as used herein refers to a gene that is easily detectable when expressed, for example, via chemiluminescence, fluorescence, colorimetric reactions, antibody binding, inducible markers, ligand binding assays, and the like. Exemplary reporter genes include but are not limited to green fluorescent protein. The production of recombinant nucleic acids, vectors, transformed host cells, proteins and protein fragments by genetic engineering is well known.

If desired, the vector may optionally contain flanking nucleic sequences that direct site-specific homologous recombination. The use of flanking DNA sequences to permit homologous recombination into a desired genetic locus is known in the art. At present it is preferred that up to several kilobases or more of flanking DNA corresponding to the chromosomal insertion site be present in the vector on both sides of the encoding sequence (or any other sequence of this invention to be inserted into a chromosomal location by homologous recombination) to assure precise replacement of chromosomal sequences with the exogenous DNA. See e.g. Deng et al, 1993, Mol. Cell. Biol 13(4):2134-40; Deng et al, 1992, Mol Cell Biol 12(8):3365-71; and Thomas et al, 1992, Mol Cell Biol 12(7):2919-23. It should also be noted that the cell of this invention may contain multiple copies of the gene of interest.

Transformed host cells are cells which have been transformed or transfected with vectors containing nucleic acid constructs of the invention and may or may not transcribe or translate the operatively associated nucleic acid of interest.

RNA Interference Cassette for Customization of Animal Traits

In another embodiment, the present invention provides a transgenic animal with customizable traits, wherein the genome of the transgenic animal comprises:

an exogenous inhibitory RNA coding sequence of interest, operably linked to a promoter and under the control of an inducible gene expression system that requires the presence of an inducing agent to activate gene expression;

wherein the expression of the exogenous inhibitory RNA coding sequence of interest is inhibited in the absence of the inducing agent.

In certain embodiments, the exogenous inhibitory RNA coding sequence of interest interferes with the expression of a nucleic acid sequence encoding pigment proteins; proteins involved in the synthesis and/or transport of pigments; proteins involving the length and/or texture of animal skin or fur; luminescent (such as fluorescent) proteins; and proteins involved in the texture, structural strength, and/or length of animal nail, claw, or horn texture.

In one embodiment, an exogenous inhibitory RNA coding sequence encodes an siRNA that interferes with the expression of cross-linking actin) in the nails, thereby producing genetically-engineered animals (such as cats) with nails that are soft instead of sharp.

In one embodiment, the RNAi construct comprises an siRNA that interferes with the expression of a nucleic acid molecule encoding cross-linking keratin), operably linked to a promoter specific to the cross-linking keratin, and is under the control of a reporter gene flanked by loxP sites.

Keratin proteins involved in the texture, structural strength, and/or length of animal hair, nail, claw and/or horn include, but are not limited to, keratin 1, keratin 2, keratin 2A, keratin HB6, keratin 3, keratin 4, keratin 5, keratin 6, keratin 7, keratin 8, keratin 9, keratin 10, keratin 11, keratin 12, keratin 13, keratin 14, keratin 15, keratin 16, keratin 17, keratin 18, keratin 19, keratin 20, keratin 23, keratin 24, keratin 25, keratin 26, keratin 27, keratin 28, keratin 31, keratin 32, keratin 33, keratin 34, keratin 35, keratin 36, keratin 37, keratin 38, keratin 39, keratin 40, keratin 71, keratin 72, keratin 73, keratin 74, keratin 75, keratin 76, keratin 77, keratin 78, keratin 79, keratin 80, keratin 81, keratin 82, keratin 83, keratin 84, keratin 85, and keratin 86.

In one embodiment, the present invention provides a microRNA cassette comprising the siRNA coding sequence and a 3' UTR sequence.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as PKC-t.

As used herein, the team "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., PKC-t mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide," refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

Methods of Making Transgenic Non-Human Animals

Any of various methods can be used to introduce a transgene into a non-human animal to produce a transgenic animal. Such techniques are well-known in the art and include, but are not limited to, pronuclear microinjection, viral infection and transformation of embryonic stem cells and iPS cells. Methods for generating transgenic animals that can be used include, but are not limited to, those described in J. P. Sundberg and T. Ichiki, Eds., Genetically Engineered Mice Handbook, CRC Press; 2006; M. H. Hofker and I. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; 2002, ISBN-10: 0879695919; K. Turksen (Ed.), Embryonic stem cells: methods and protocols in Methods Mol. Biol. 2002; 185, Humana Press; Current Protocols in Stem Cell Biology, ISBN: 978047015180; Meyer et al. PNAS USA, vol. 107 (34), 15022-15026.

In certain embodiments, the genetically engineered animals with site-specific knock-ins can be created using spermatogonial stem cells (SSCs), PiggyBac™ mobile DNA technology using transposable elements, *Xanthamonas* transcription activator-like (TAL) Nucleases (XTNs) [aka TAL-effector nucleases (TALENs)], and a combination thereof.

Methods for Customizing Animal Traits

In one embodiment, the present invention provides a method of customizing animal traits using the transgenic animal of the invention. In one embodiment, the method comprises:

a) providing a transgenic animal whose genome comprises:
an exogenous nucleic acid molecule encoding a protein of interest, wherein the nucleic acid molecule is operably linked to a promoter and is under the control of an inducible gene expression system that requires the presence of an inducing agent to activate gene expression;
wherein the expression of the exogenous nucleic acid molecule is inhibited in the absence of the inducing agent;
b) administering the inducing agent to the transgenic animal thereby inducing the expression of the exogenous nucleic acid molecule.

In certain embodiments, the exogenous nucleic acid molecule encodes a protein of interest, wherein the protein of interest is selected from pigment proteins; proteins involved in the synthesis and/or transport of pigments; luminescent (such as fluorescent) proteins; proteins involving the length and/or texture of animal skin or fur; and proteins involved in the texture, structural strength, and/or length of animal nail, claw, and/or horn.

In certain embodiments, the inducible gene expression systems useful according the present invention include, but are not limited to, site-specific recombination systems including, but not limited to, a Cre-LoxP recombination system, a FLP-FRT recombination system; a tetracycline (Tet)-controlled transcription activation system; an ecdysone inducible system; a heat shock on/off system; a lacO/IPTG system; a cumate repressor protein CymR system; a nitroreductase system; coumermycin/novobiocin-regulated system; a RheoSwitch Ligand RSL1 system; a chimeric bipartite nuclear receptor expression system; a GAL4 system; sterol or steroid or synthetic steroid inducing/repressing system; and any combinations thereof.

In certain embodiments, the inducing agents for gene expression useful according the present invention include, but are not limited to, cre recombinase, HTCre; FLP recombinase; tetracycline or its derivatives such as doxycycline; ecdysone; cumate; nitroreductase steroids; and any combinations thereof.

In one embodiment, the transgenic animal comprises an exogenous nucleic acid molecule that is under the control of a site-specific recombination system, and the expression of the exogenous nucleic acid molecule is induced after the administration (such as via topical administration) of a recombinase protein, or the administration (such as via injection) of a nucleic molecule encoding a recombinase protein, to the transgenic animal.

In one embodiment, the genome of the transgenic animal comprises an exogenous nucleic acid molecule whose expression is under the control of a Cre/LoxP recombination system, wherein the Cre/LoxP recombination system prevents the expression of the exogenous nucleic acid molecule, wherein the administration (such as via topical administration) of Cre recombinase and/or HTCre, or the administration (such as via injection) of a nucleic molecule encoding Cre recombinase and/or HTCre, to the transgenic animal, induces the expression of the exogenous nucleic acid molecule, thereby customizing the animal trait(s) of interest.

In another specific embodiment, the method of customizing animal traits comprises:
  a) providing a transgenic animal whose genome comprises:
    a first exogenous nucleic acid molecule encoding a protein of interest (such as pigmentation protein) operably linked to a first promoter and under the control of a loxP site, wherein the loxP site prevents the expression of the first nucleic acid molecule in the absence of Cre recombinase protein;
    a second nucleic acid encoding a reverse tTA (rtTA), operably linked to a second promoter; and
    a third nucleic acid molecule encoding a Cre recombinase protein, operably linked to a third promoter under the control of a TetO operator;
  b) administering doxycycline to the transgenic animal, thereby inducing the expression of the exogenous nucleic acid molecule.

The inducing agent for administration to the transgenic animal can be in a form that can be combined with a carrier. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

The inducing agent and compositions can be administered to the transgenic animal by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a transgenic animal.

EXAMPLES

Following are examples that illustrate procedures and embodiments for practicing the invention. The examples should not be construed as limiting.

Example 1—Customization of Skin or Fur Pigmentation in Animals

This Example provides embodiments of genetic constructs for customizing skin and fur pigmentation in animals. Animals with Customized Pigmentation and Pattern in the Skin or Fur C3H/HeJ murine strain with a brown ("Agouti" coloration) skin color are genetically engineered to express the following three constructs: 1) a construct comprising a keratin-14 specific promoter, a loxp cassette comprising a nucleic acid encoding a red fluorescent protein, a pigment cassette comprising a nucleic acid encoding a dominant black ($\Delta$G23) beta defensin 103 protein, and an SV40 (with intron) polyadenylation sequence; 2) a construct comprising a nucleic acid molecule encoding a reverse tetracycline transactivator operably linked to a keratin-14 specific promoter that initiates the transcription of the nucleic acid encoding rtTA, and an SV40 polyadenylation sequence; and 3) a construct comprising an agouti signaling protein (ASP), operably linked to a tetracycline-sensitive promoter (TetO)7 that initiates the transcription of the nucleic acid molecule encoding ASP, and a bovine growth hormone (BGH) polyadenylation sequence.

When doxycycline is fed to the genetically-modified mice, mouse fur turns golden (this is the first demonstration of genetic modification of hair color after birth). The application of Cre or HTNCre to the shaved skin of the genetically-engineered mice, via a carrier base (e.g., protein carriers, such as lipid bilayers), induces genetically permanent black coloration of fur in the area where Cre and/or HTNCre is applied. In accordance with the present invention, mice born with brown fur can be modified to have golden fur with arbitrarily shaped black markings. For example, a black name or black logo can be created on mice fur with a gold background.

To customize skin pigmentation in animals, the animal could only express a pigmentation construct, and need not express a patterning construct (as shown in FIG. 2). The customization of pigmentations and patterns is activated directly by application of Cre and/or HTNCre.

In one embodiment heritable patterns can be created by genetically modifying the animals to express a patterning construct. FIG. 2 shows one embodiment of a patterning construct. The promoter can be the Ripply2 promoter, or from any gene specific to somite boundary specification. Alternate promoters could be the Tabby or Ticked promoters.

In one embodiment, the genetically-modified animal, whose genome comprises a pigmentation construct and a patterning construct, has constitutive vertical stripes on the dorsal dermis.

Complex/Multicolored Patterns

FIG. 3 illustrates certain embodiments of genetic constructs for creating complex or multicolored patterns in animal skin or fur. In one embodiment, complex patterns can be created with the use of a construct comprising an inducible system, such as promoters with mechanisms of inducibility. As shown in FIG. 3, Cre is activated by the presence of doxycycline only in tissues specific for the rtTA promoter. The use of tissue-specific promoter maintains somite border in animals; for example, the transgene can only be activated during the developmental period. Inducible system can also be used to create multiple colors.

Inducible systems useful according to the present invention include, but are not limited to, tetracycline, ecdysone, and tamoxifen inducible systems; FLP-FRT recombination system; and Cre-LOX recombination system.

Example 2—Mice with Customized Fur Color and Pattern

This Example shows the creation of genetically-modified mice whose fur color can be permanently altered through the transdermal application of HTNCre—a recombinase that can easily cross cell membranes.

Figure 4:
FIG. 4 is a schematic depiction of one embodiment of a genetic construct for creating customizable patterns and color in the skin or fur of mice. The construct comprises a Keratin14 promoter, which is expressed in all skin fibroblasts, to drive the dominant black form of signaling molecule β-Def103. The expression of β-Def103 is blocked by a LoxP excisable nucleic acid encoding ring finger protein (RFP), which is used as a marker. The nucleic acid molecule encoding RFP is not required for the construct, and can be replaced by STOPs.

FIG. 4 shows a genetic construct for creating customized patterns and color in mouse skin or fur. The construct comprises a Keratin14 promoter, which is expressed in all skin fibroblasts, to drive the dominant black form of signaling molecule beta-Def103; the expression of beta-Def103 is blocked by a Loxp excisable nucleic acid encoding ring finger protein (RFP) (the RFP is used as a marker).

Agouti mice are genetically-engineered to express a transgene encoding the "dominant black" signaling molecule βDef103, and the transgene expression is activated by the application of recombinase.

Figure 5A:
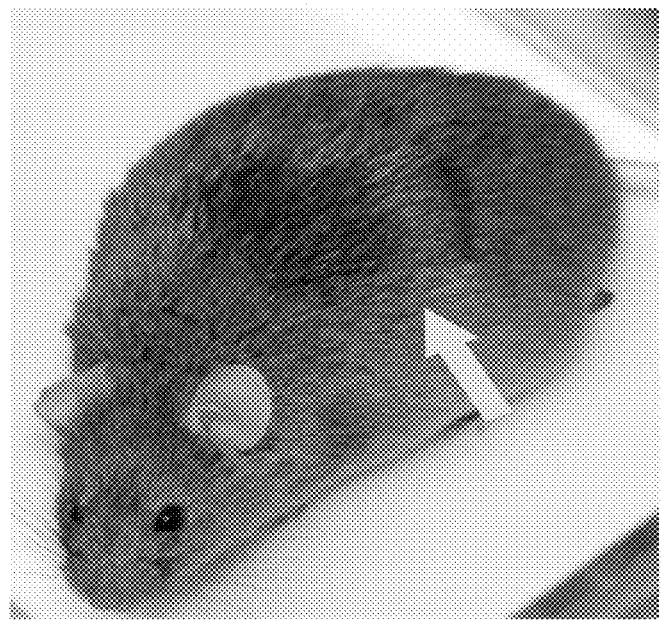
FIG. 5 (A) shows that beta-Def103 expression activated by transdermal application of recombinase creates a genetically permanent alteration in the coat or fur of an adult mouse. (B) Fine control of marking alteration can be achieved: a mouse with a single narrow black line is created by injection of recombinase. The change in skin/fur pattern has persisted through multiple cycles of coat regrowth, indicating successful alteration of resident stem cells.
Figure 5B:

FIGS. 5A and B are photographs that show two genetically-engineered mice in which the expression of the dominant black pigment protein is activated by dermal or intradermal application of HTNCre in a carrier solution. Before the present invention, recombinase has never been applied in live animals.

Figure 6:
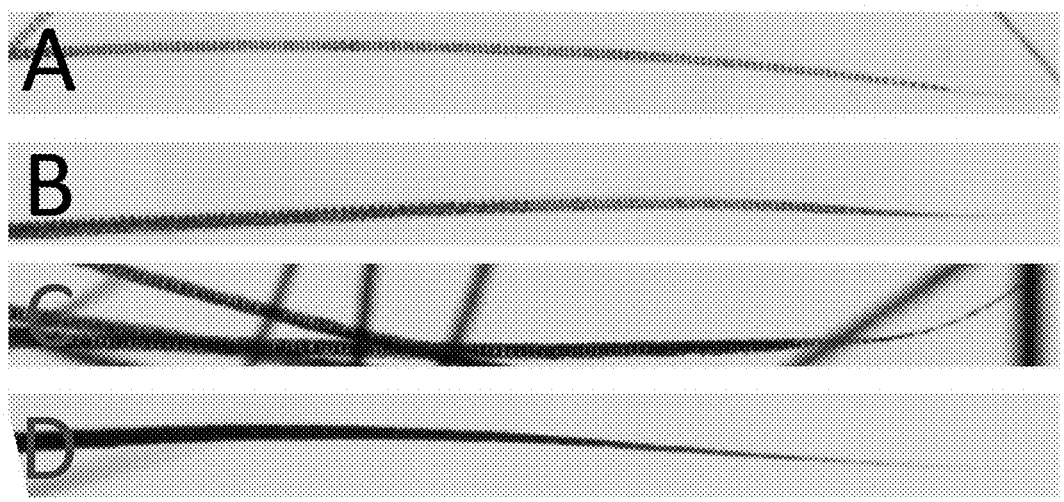
FIG. 6 shows that coat color of the transgenic mice can be titrated through the amount of recombinase applied to the mouse skin. Increasing the amounts of recombinase applied to the mice increases the level of transgene expression and eumelanin activation.

FIG. 6 shows that the application of recombinase to genetically-engineered mice can result in dose dependent change in fur color. The tip of Agouti mouse hairs are normally characterized by cells comprising yellow pheomelanin (A). As shown in FIG. 6, through increasing activation of the transgene by increasing recombinase doses, the mouse fur pigments can be shifted to a mix of pheomelanin and black eumelanin (B) to pure eumelanin (C) to so much melanin that the compartmentalized structure breaks down (D). This Example shows that transdermal application of recombinase can result in fine control of hair color in genetically-engineered mice.

Example 3—Customized Skin Color and Pattern for Cattle Identification

In the cattle industry, a robust method of birth processing for individual identification has become increasingly important for proof of ownership, herd management, tracking of animal movements, and perhaps, most importantly, animal disease traceability.

This Example provides transgenic cattle having customized skin color and patterns that can be used as a code (e.g., bar code) for cattle identification. The transgenic cattle can be created using the method described in Example 2. As shown in Example 2, transdermal or intradermal application of recombinase to transgenic mice whose genomic comprises a Cre-LoxP recombination system induce customizable changes in coat color after birth.

Figure 7:
FIG. 7 is a schematic depiction of one embodiment of a genetic construct for knock-in cattle with spermatozoa-specific expression of enhanced green fluorescent protein (EGFP), and recombinase-mediated melanocyte-specific expression of a dominant negative Rab7. A nucleic acid sequence encoding neomycin resistance biomarker protein, which can be excised through PIGGYBAC™ transposons, is placed in the center of the construct, and the construct is flanked by short homology arms.

FIG. 7 shows a construct design for creating customized pattern or color identification in cattle. The construct comprises a nucleic acid molecule encoding a dominant negative Rab7, operably linked to a MC1R promoter and under the control of the loxP-STOP-loxP sequence. The expression of the Rab7 can be induced by the application of Cre recombinase. The use of TAL nucleases allows site-specific knock-ins with short homology arms. The acrosin promoter/EGFP arm on the construct allows flow sorting for genetically modified sperm, thereby ensuring 100% genetically modified offspring in the F1 generation. An important element for the construct is the MC1R (melanocortin receptor) promoter, which drives the expression of a dominant negative Rab7 gene only when activated with recombinase. The combination of various elements in the construct allows creation of cattle modified with site-specific knock-in(s) that allows creation of permanent identification information on cattle.

Figure 8:
FIG. 8 shows a depiction of a Black Angus heifer genetically engineered to express a customizable identification pattern in the skin.

FIG. 8 shows a depiction of a Black Angus heifer genetically engineered to express a customizable identification pattern in the skin.

During birth processing, individual identification information can be easily created by applying Cre recombinase to cattle whose genome comprises the construct shown in FIG. 7. Also, the transgenes are only expressed in the animal skin, which can be removed during food processing; therefore, the creation of cattle identification in the animal skin should not raise regulatory issues with governmental agencies such as USDA.

In certain embodiments, site-specific knock-in animals can be created using conventional technologies, including, but not limited to, spermatogonial stem cells (SSCs), PiggyBac™ mobile DNA technology using transposable elements, *Xanthamonas* transcription activator-like (TAL) Nucleases (XTNs) [aka TAL-effector nucleases (TALENs)], and a combination thereof.

In one embodiment, Black Angus coat color is postnatally modified with a heterozygous knock-in using a melanocyte-specific dominant negative Rab7, which is required for intracellular transport of the critical melanogenesis gene Tyrp1.

Example 4—Customized Skin Color and Pattern for Cattle Disease Detection

Diseases are a concern for nearly every beef and dairy producer, and many common diseases can dramatically impact production without having overt clinical signs. Sudden death is often the first and only sign of clostridial diseases. Subclinical mastitis is a common and expensive problem in dairy production. Even rumors of bovine spongioform encephalopathy (BSE), which rarely has overt clinical signs, can cause severe economic damage to beef industry. In addition to infectious diseases, metabolic diseases in cattle can also cause economic damages: ⅓ of beef cattle have subclinical copper deficiency due to the presence of chelating agents in their diet. Changes in fur or skin color, in accordance with the present invention (e.g., using recombinase-activated coat-color specific markers) can be used to identify the presence of diseases in cattle.

In one embodiment, the construct for cattle disease detection is identical to the construct as shown in FIG. 7, except that the MC1R promoter is replaced with an alternate recombinase system (e.g., Flp-Frt recombination system) and/or disease-specific promoters, such as promoters responsive to NFkB, Ifnγ, or copper-deficiency targets.

In one embodiment, during birth processing, cattle are painted with the recombinase to create the desired symbol.

The painted area would change color once the cattle develop inflammatory or metabolic stresses (the expression of pigment protein regulated by disease-specific promoter). The cattle disease detection application can be used in combination with the cattle identification application through the use of different recombinases and recombinase targets.

Example 5—Dogs with Customizable Coats

Different dog breeds have coat color as a result of different combinations of mutations in pigment genes. Pugs have an intact melanocortin receptor with no endogenous expression of the "dominant black" signaling molecule βDef103.

Dogs with customized fur color and pattern can be created using the methods described in Examples 3 and 4 for cattle, or through the process shown in Example 2 for mice. In one embodiment, genetically-engineered pugs whose genome comprises the construct as shown in FIG. 7 have fur with customizable color and pattern including tiger stripes, logos, writing, and hearts.

Dogs are normally difficult to genetically engineer due to the oddities in the egg development system in canines. Currently, genetically-engineered dogs cannot be created by in vitro fertilization (IVF). Genetically-engineered dogs with site-specific knock-ins can be created using spermatogonial stem cells (SSCs), PiggyBac™ mobile DNA technology using transposable elements, *Xanthamonas* transcription activator-like (TAL) Nucleases (XTNs) [aka TAL-effector nucleases (TALENs)], and a combination thereof.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

1. Candille S I, Kaelin C B, Cattanach B M, Yu B, Thompson D A, Nix M A, Kerns J A, Schmutz S M, Millhauser G L, and Barsh G S. A-defensin mutation causes black coat color in domestic dogs. *Science* 318: 1418-1423, 2007.
2. Kistner et al., Doxycycline-mediated quantitative and tissue-specific control of gene expression in transgenic mice, *Proc. Natl. Acad. Sci. U.S.A.* Vol. 93, pp. 10933-10938, 1996.
3. Nolden L, Edenhofer F, Haupt S, Koch P, Wunderlich F T, Siemen H, and Brustle O. Site-specific recombination in human embryonic stem cells induced by cell-permeant Cre recombinase. *Nat Methods* 3: 461-467, 2006.
4. Nagy, Cre recombinase: the universal reagent for genome tailoring, *Genesis* 26:99-109, 2000.

I claim:

1. A method of customizing a trait in a non-human animal comprising:
   providing a non-human transgenic animal comprising in its genome an inducible expression system, the inducible expression system comprising:
   an exogenous nucleic acid molecule operably linked to a promoter,
   wherein the promoter is selected from keratinocyte specific promoters and melanocyte specific promoters;
   a nucleic acid sequence present between the promoter and the exogenous nucleic acid molecule, which nucleic acid sequence blocks the expression of the exogenous nucleic acid molecule; and
   an inducing agent administered to the skin of the animal by intradermal injection, which inducing agent interacts with the nucleic acid sequence that blocks expression of the exogenous nucleic acid molecule and deletes the exogenous nucleic acid sequence that blocks expression of the exogenous nucleic acid molecule such that the exogenous nucleic acid molecule is expressed;
   wherein the exogenous nucleic acid molecule encodes β-defensin 103; and
   administering the inducing agent by intradermal injection thereby inducing the expression of β-defensin 103 in keratinocytes and/or melanocytes;
   wherein the expression of β-defensin 103 in keratinocytes and/or melanocytes that received the inducing agent causes a phenotypic change in skin and/or fur pigmentation.

2. The method according to claim 1, wherein the nucleic acid present between the promoter and the exogenous nucleic acid molecule comprises a Cre-LoxP recombination system and wherein the inducing agent is Cre.

3. The method according to claim 1, wherein the exogenous nucleic acid molecule is transferred into the animal via the use of spermatogonial stem cells (SSCs), piggyBac™ mobile DNA technology using transposable elements, Xanthamonas transcription activator-like (TAL) Nucleases (XTNs), or a combination thereof.

* * * * *